US012637462B2

(12) United States Patent
Cha et al.

(10) Patent No.: US 12,637,462 B2
(45) **Date of Patent: *May 26, 2026**

(54) INTEGRIN INHIBITOR AND USES THEREOF

(71) Applicant: Pliant Therapeutics, Inc., South San Francisco, CA (US)

(72) Inventors: Jacob Cha, San Bruno, CA (US); Katerina Leftheris, San Mateo, CA (US); Qi Gao, Franklin Park, NJ (US); Jian Wang, Branchburg, NJ (US); Dalian Zhao, Fanwood, NJ (US)

(73) Assignee: Pliant Therapeutics, Inc., South San Francisco, CA (US)

( * ) Notice: Subject to any disclaimer, the term of this patent is extended or adjusted under 35 U.S.C. 154(b) by 244 days.

This patent is subject to a terminal disclaimer.

(21) Appl. No.: 18/619,017

(22) Filed: Mar. 27, 2024

(65) Prior Publication Data

US 2024/0391914 A1 Nov. 28, 2024

Related U.S. Application Data

(63) Continuation of application No. 17/531,074, filed on Nov. 19, 2021, now Pat. No. 12,018,025.

(60) Provisional application No. 63/116,042, filed on Nov. 19, 2020.

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC .................................................... C07D 471/04
USPC ..................................................... 514/266.21
See application file for complete search history.

(56) References Cited

U.S. PATENT DOCUMENTS

| | | | | |
|---|---|---|---|---|
| 10,131,658 | B2 | 11/2018 | Degrado | |
| 10,214,522 | B2 | 2/2019 | Degrado | |
| 10,604,520 | B2 | 3/2020 | Jiang | |
| 10,696,672 | B2 | 6/2020 | Morgans, Jr. | |
| 10,793,564 | B2 | 10/2020 | Cha | |
| 11,180,494 | B2 | 11/2021 | Cha et al. | |
| 11,396,506 | B2 | 7/2022 | Leftheris et al. | |
| 11,419,869 | B2 | 8/2022 | Decaris et al. | |
| 11,560,376 | B2 * | 1/2023 | Cha | C07D 471/04 |
| 11,584,738 | B2 | 2/2023 | Bestvater et al. | |
| 11,634,418 | B2 | 4/2023 | Morgans, Jr. et al. | |
| 11,673,887 | B2 | 6/2023 | Jiang et al. | |
| 11,858,931 | B2 | 1/2024 | Leftheris | |
| 11,952,376 | B2 | 4/2024 | Cha | |
| 12,018,025 | B2 | 6/2024 | Cha | |
| 12,134,642 | B2 | 11/2024 | Andre et al. | |
| 12,390,463 | B2 | 8/2025 | Decaris et al. | |
| 2008/0108637 | A1 | 5/2008 | Fujita et al. | |
| 2013/0005782 | A1 | 1/2013 | Chigaev et al. | |
| 2014/0038910 | A1 | 2/2014 | Ruminski et al. | |
| 2016/0244447 | A1 | 8/2016 | Askew et al. | |
| 2016/0264566 | A1 | 9/2016 | Degrado | |
| 2016/0317527 | A1 | 11/2016 | Askew et al. | |
| 2016/0376266 | A1 | 12/2016 | Degrado | |
| 2017/0306026 | A1 | 10/2017 | Taylor et al. | |
| 2017/0313708 | A1 | 11/2017 | Furuya et al. | |
| 2018/0093984 | A1 | 4/2018 | Jiang | |
| 2018/0282327 | A1 | 10/2018 | Furuya | |
| 2018/0303902 | A1 | 10/2018 | Cochran et al. | |
| 2019/0276449 | A1 | 9/2019 | Cha | |
| 2019/0322663 | A1 | 10/2019 | Morgans, Jr. et al. | |
| 2020/0109141 | A1 | 4/2020 | Cha | |
| 2020/0123151 | A1 | 4/2020 | Leftheris et al. | |
| 2020/0352942 | A1 | 11/2020 | Cha et al. | |
| 2021/0017171 | A1 | 1/2021 | Cha et al. | |
| 2021/0024516 | A1 | 1/2021 | Jiang | |
| 2021/0122747 | A1 | 4/2021 | Morgans, Jr. et al. | |
| 2021/0147526 | A1 | 5/2021 | Andre et al. | |
| 2022/0144829 | A1 | 5/2022 | Cha et al. | |
| 2022/0177468 | A1 | 6/2022 | Cha et al. | |
| 2022/0289743 | A1 | 9/2022 | Leftheris et al. | |
| 2023/0028658 | A1 | 1/2023 | Turner et al. | |
| 2023/0117605 | A1 | 4/2023 | Decaris et al. | |
| 2023/0181546 | A1 | 6/2023 | Lefebvre et al. | |
| 2023/0271960 | A1 | 8/2023 | Cha et al. | |

(Continued)

FOREIGN PATENT DOCUMENTS

| | | | |
|---|---|---|---|
| WO | 2015048819 | A1 | 4/2015 |
| WO | 2016145258 | A1 | 9/2016 |

(Continued)

OTHER PUBLICATIONS

Alhazzani, W. et al. (Mar. 28, 2020). "Surviving Sepsis Campaign: Guidelines on the Management of Critically Ill Adults with Coronavirus Disease 2019 (COVID-19)," Intensive Care Medicine 46(5):854-887.

Database Pubchem Substance Anonymous: "SCHEMBL22074548", XP055937800.

Decaris, M. et al. (May 1, 2019). "Dual [alpha]V[beta]6/[alpha]V[beta]1 Inhibitor PLN-74809 Reduces Fibrogenesis in Ex Vivo and In Vivo Models of IPF: D17. Towards the Next IPF Therapies," American Journal of Respiratory and Critical Care Medicine, pp. 2-2.

Decision to grant a European patent, dated Nov. 3, 2023, for European Patent Application No. 19765136.7, 2 pages.

(Continued)

*Primary Examiner* — Niloofar Rahmani

(74) *Attorney, Agent, or Firm* — Morrison & Foerster LLP; Kraig Anderson; Johannes Hull

(57) ABSTRACT

Provided herein are integrin inhibitors, compositions thereof, and methods of their uses. Crystalline forms of salts of the inhibitors are also described, along with methods of preparing the crystalline forms. X-ray powder diffraction data, thermogravimetric analysis, and differential scanning calorimetry data are provided for the crystalline forms. The integrin inhibitors are useful for treatment of, inter alia, fibrotic diseases.

26 Claims, 12 Drawing Sheets

(56) References Cited

U.S. PATENT DOCUMENTS

| | | | |
|---|---|---|---|
| 2023/0293519 A1 | 9/2023 | Lefebvre et al. |
| 2023/0365556 A1 | 11/2023 | Jiang et al. |
| 2024/0043421 A1 | 2/2024 | Morgans, Jr. |
| 2024/0122930 A1 | 4/2024 | Lefebvre |
| 2024/0245682 A1 | 7/2024 | Machajewski |
| 2024/0270742 A1 | 8/2024 | Cha et al. |
| 2024/0294520 A1 | 9/2024 | Leftheris et al. |
| 2024/0350494 A1 | 10/2024 | Turner et al. |
| 2025/0026819 A1 | 1/2025 | Andre et al. |

FOREIGN PATENT DOCUMENTS

| | | |
|---|---|---|
| WO | 2018049068 A1 | 3/2018 |
| WO | 2018119087 A1 | 6/2018 |
| WO | 2018160521 A2 | 9/2018 |
| WO | 2018160522 A1 | 9/2018 |
| WO | 2018160521 A3 | 10/2018 |
| WO | 2019173653 A1 | 9/2019 |
| WO | 2020006315 A1 | 1/2020 |
| WO | 2020047207 A1 | 3/2020 |
| WO | 2020047208 A1 | 3/2020 |
| WO | 2020047239 A1 | 3/2020 |
| WO | 2020076862 A1 | 4/2020 |
| WO | 2020210404 A1 | 10/2020 |
| WO | 2021097338 A1 | 5/2021 |
| WO | 2021225912 A1 | 11/2021 |
| WO | 2022087224 A1 | 4/2022 |
| WO | 2022109598 A1 | 5/2022 |
| WO | 2022232838 A1 | 11/2022 |
| WO | 2023035000 A1 | 3/2023 |
| WO | 2023064943 A1 | 4/2023 |
| WO | 2023225119 A1 | 11/2023 |
| WO | 2024015717 A2 | 1/2024 |
| WO | 2024155965 A2 | 7/2024 |

OTHER PUBLICATIONS

Desu, H.R. et al. (Mar. 13, 2018). "Nebulization of Cyclic Arginine-Glycine-(D)-Aspartic Acid-Peptide Grafted and Drug Encapsulated Liposomes for Inhibition of Acute Lung Injury," Pharmaceutical Research 35(5)94, pp. 1-15.
Extended European Search Report, dated Mar. 12, 2025, for European Patent Application No. 24207882.2, 7 pages.
Extended European Search Report, dated Sep. 6, 2024, for European Patent Application No. 21895890.8, 7 pages.
Extended European Search Report, dated Sep. 24, 2021, for European Patent Application No. 19765136.7, 7 pages.
Horan, S.G. et al. (Jan. 1, 2008). "Partial Inhibition of Integrin Alpha(v)Beta6 Prevents Pulmonary Fibrosis Without Exacerbating Inflammation," American Journal of Respiratory and Critical Care Medicine 177(1):56-65.
Intention to grant, dated Apr. 14, 2023, for European Patent Application No. 19765136.7, 6 pages.
Intention to grant, dated Sep. 14, 2023, for European Patent Application No. 19765136.7, 6 pages.
International Preliminary Report on Patentability mailed on Jun. 1, 2023 for PCT Application No. PCT/US2021/072510 filed on Nov. 19, 2021, 8 pages.
International Preliminary Report on Patentability mailed on Sep. 17, 2020 for PCT Application No. PCT/US2019/021243 filed on Mar. 7, 2019, 7 pages.
International Preliminary Report on Patentability received for PCT Patent Application No. PCT/US2022/072013, mailed on Nov. 9, 2023, 8 pages.
International Search Report and Written Opinion of the International Searching Authority mailed on Feb. 18, 2022, for PCT Application No. PCT/US2021/072510 filed on Nov. 19, 2021, 9 pages.
International Search Report and Written Opinion received for PCT Patent Application No. PCT/US2022/072013, mailed on Jul. 14, 2022, 09 pages.
International Search Report and Written Opinion received for PCT Patent Application No. PCT/US2022/075954, mailed on Nov. 30, 2022, 09 pages.
Invitation to Pay Additional Fees mailed on Jul. 20, 2021 for PCT Application No. PCT/US2021/030363 filed on Apr. 30, 2021, 2 pages.
Invitation to Pay Additional Fees mailed on Oct. 27, 2023 for PCT Application No. PCT/US2023/069826 filed on Jul. 7, 2023, 3 pages.
Invitation to Pay Additional Fees received for PCT Patent Application No. PCT/US2022/078175, mailed on Nov. 25, 2022, 2 pages.
Lukey, P.T. et al. (2020, e-pub. Dec. 9, 2019). "Clinical Quantification of the Integrin [alpha]v[beta]6 by [F]FB-A20FMDV2 Positron Emission Tomography in Healthy and Fibrotic Human Lung (PETAL Study)," European Journal of Nuclear Medicine and Molecular Imaging 47(4):967-979.
Maher, T.M. et al. (Mar. 26, 2020). "A Positron Emission Lomography Imaging Study to Confirm Target Engagement in the Lungs of Patients with Idiopathic Pulmonary Fibrosis Following a Single Dose of a Novel Inhaled [alpha]v[beta]6 Integrin Inhibitor," Respiratory Research 21(75):9 pages.
Onega, M. et al. (Jan. 3, 2020). "Preclinical Evaluation of [18F] FB-A20FMDV2 as a Selective Marker for Measuring aVβ6 Integrin Occupancy Using Positron Emission Tomography in Rodent Lung," European Journal of Nuclear Medicine and Molecular Imaging 47(4):958-966.
Pliant Therapeutics. (Feb. 13, 2025). "Pliant Therapeutics Announces Next Steps Following DSMB Recommendations on Beacon-IPF, A Phase 2b/3 Trial in Patents With Idiopathic Pulmonary Fibrosis," Pliant Therapeutics, 1 page.
Pliant Therapeutics. (Feb. 7, 2025). "Pliant Therapeutics Provides Update on Beacon-IPF, A Phase 2b/3 Trials in Patients With Idiopathic Pulmonary Fibrosis," Pliant Therapeutics, 1 page.
Pliant Therapeutics. (Mar. 3, 2025). "Pliant therapeutics Provides Update on Beacon-IPF, a Phase 2b/3 Trial in patients With Idiopathic Pulmonary Fibrosis," Pliant Therapeutics, 2 pages.
Raghu, G. et al. (Jul. 14, 2018). "Randomized, Double-Blind, Placebo-Controlled, Multiple Dose, Dose-Escalation Study of BG00011 (Formerly STX-100) in Patients with Idiopathic Pulmonary Fibrosis (IPF)," American Journal of Respiratory and Critical Care Medicine 197:A7785.
Clarivate Analytics Record for PLN-74809 (Aug. 8, 2018)., 1 page.
International Preliminary Report on Patentability, issued May 16, 2023, mailed Feb. 18, 2022 for PCT Application No. PCT/US2021/072510, filed Nov. 19, 2021, 7 pages.
International Search Report and Written Opinion, mailed Feb. 18, 2022, for PCT Application No. PCT/US2021/72510, filed Nov. 19, 2021, 10 pages.
Kim, D.S. et al. (2006). "Classification and Natural History of the Idiopathic Interstitial Pneumonias," Proc. Am. Thorac. Soc. 3:285-292.
Kinder, B.W. et al. (Jun. 2007). "Idiopathic Nonspecific Interstitial Pneumonia. Lung Manifestation of Undifferentiated Connective Tissue Disease?," Am. J. Respir. Crit. Care Med. 176:691-697.
Lynch, D. (2001, e-pub. Dec. 1, 2001). "Nonspecific Interstitial Pneumonia: Evolving Concepts," Radiology 221(3):583-584.
PubChem. (Dec. 16, 2018). "Bexotegrast," PubChem CID 135390719, 19 pages.
Pubmed Compound Record for CID 135390719 (Dec. 16, 2018). "Unii-qcv154pft4,", 9 pages.

* cited by examiner

INTEGRIN INHIBITOR AND USES THEREOF

CROSS REFERENCE TO RELATED APPLICATIONS

This application is a continuation of U.S. Non-Provisional patent application Ser. No. 17/531,074, filed on Nov. 19, 2021, which claims the benefit of priority to U.S. Provisional Application No. 63/116,042, filed Nov. 19, 2020, the entire contents of which are hereby incorporated by reference herein.

FIELD

Provided herein are integrin inhibitors, compositions thereof, and methods of their uses.

BACKGROUND

Fibrosis, a pathologic feature of many diseases, is caused by a dysfunction in the body's natural ability to repair damaged tissues. If left untreated, fibrosis can result in scarring of vital organs causing irreparable damage and eventual organ failure.

Patients with nonalcoholic fatty liver disease (NAFLD) may progress from simple steatosis to nonalcoholic steatohepatitis (NASH) and then fibrosis. While liver fibrosis is reversible in its initial stages, progressive liver fibrosis can lead to cirrhosis.

Fibrosis in the kidney, characterized by glomerulosclerosis and tubulointerstitial fibrosis, is the final common manifestation of a wide variety of chronic kidney diseases (CKD). Irrespective of the initial causes, progressive CKD often results in widespread tissue scarring that leads to destruction of kidney parenchyma and end-stage renal failure, a devastating condition that requires dialysis or kidney replacement.

Scleroderma encompasses a spectrum of complex and variable conditions primarily characterized by fibrosis, vascular alterations, and autoimmunity. The scleroderma spectrum of disorders share the common feature of fibrosis, resulting in hardening or thickening of the skin. For some patients, this hardening occurs only in limited areas, but for others, it can spread to other major organs.

Following myocardial infarction, cardiac structural remodeling is associated with an inflammatory reaction, resulting in scar formation at the site of the infarction. This scar formation is a result of fibrotic tissue deposition which may lead to reduced cardiac function and disruption of electrical activity within the heart.

Crohn's Disease is a chronic disease of unknown etiology tending to progress even in the setting of medical or surgical treatment. Intestinal fibrosis is among the most common complications of Crohn's disease, resulting in stricture formation in the small intestine and colon.

Idiopathic pulmonary fibrosis (IPF) is a chronic, progressive, fibrosing disease of unknown etiology, occurring in adults and limited to the lungs. In IPF, the lung tissue becomes thickened, stiff, and scarred. As lung fibrosis progresses, it becomes more difficult for the lungs to transfer oxygen into the bloodstream and the organs do not receive the oxygen needed to function properly. IPF currently affects approximately 200,000 people in the U.S., resulting in 40,000 deaths per year. Patients diagnosed with IPF experience progressive breathlessness and eventually, complete respiratory failure.

Primary biliary cholangitis (PBC), also known as primary biliary cirrhosis, is a chronic disease of the liver that causes damage and fibrosis in the liver. It results from a slow, progressive destruction of the small bile ducts of the liver, causing bile and other toxins to build up in the liver, a condition called cholestasis. Over time, this leads to scarring and fibrosis in both the liver and biliary tract.

Nonspecific interstitial pneumonia (NSIP) is a rare disorder that affects the tissue that surrounds and separates the tiny air sacs of the lungs. These air sacs, called the alveoli, are where the exchange of oxygen and carbon dioxide takes place between the lungs and the bloodstream. Interstitial pneumonia is a disease in which the mesh-like walls of the alveoli become inflamed. The pleura (a thin covering that protects and cushions the lungs and the individual lobes of the lungs) might become inflamed as well. There are two primary forms of NSIP—cellular and fibrotic. The cellular form is defined mainly by inflammation of the cells of the interstitium. The fibrotic form is defined by thickening and scarring of lung tissue. This scarring is known as fibrosis and is irreversible. When the lung tissue thickens or becomes scarred, it does not function as effectively. Breathing becomes less efficient, and there are lower levels of oxygen in the blood. (Kim et al., Proc. Am. Thorac. Soc. (2006) 3:285-292; Lynch, D., Radiology (2001) 221:583-584; Kinder et al., Am. J. Respir. Crit. Care Med. (2007) 176: 691-697).

Available courses of treatment are scarce, as there are currently no options on the market proven to have an effect on long-term patient survival or symptomatology. There remains a need for treatment of fibrotic diseases.

The $\alpha_v\beta_6$ integrin is expressed in epithelial cells, and binds to the latency-associated peptide of transforming growth factor-β1 (TGFβ1) and mediates TGFβ1 activation. Its expression level is significantly increased after injury to lung and cholangiocytes, and plays a critical *in vivo* role in tissue fibrosis. Increased levels are also associated with increased mortality in IPF and NSIP patients.

Primary sclerosing cholangitis (PSC) involves bile duct inflammation, and fibrosis that obliterates the bile ducts. The resulting impediment to the flow of bile to the intestines can lead to cirrhosis of the liver and subsequent complications such as liver failure and liver cancer. Expression of $\alpha_v\beta_6$ is elevated in liver and bile duct of PSC patients.

There remains a great need for agents that exploit new mechanisms of action and may have better outcomes in terms of relief of symptoms, safety, and patient mortality, both short-term and long-term. US20190276449, the content of which is incorporated herein by reference in its entirety, discloses (S)-4-((2-methoxyethyl)(4-(5,6,7,8-tetrahydro-1,8-naphthyridin-2-yl)butyl)amino)-2-(quinazolin-4-ylamino) butanoic acid, which is an $\alpha_v\beta_6$ integrin inhibitor and provides a potential treatment of fibrosis.

To move a drug candidate such as (S)-4-((2-methoxyethyl)(4-(5,6,7,8-tetrahydro-1,8-naphthyridin-2-yl)butyl) amino)-2-(quinazolin-4-ylamino)butanoic acid to a viable pharmaceutical product, it can be important to understand whether the drug candidate has crystalline forms, as well as the relative stability and interconversions of these forms under conditions likely to be encountered upon large-scale production, transportation, storage and pre-usage preparation. The ability to control and produce a stable crystalline form with a robust manufacturing process can be key for regulatory approval and marketing. Large scale production processes for high purity (S)-4-((2-methoxyethyl)(4-(5,6,7,8-tetrahydro-1,8-naphthyridin-2-yl)butyl)amino)-2-(quinazolin-4-ylamino)butanoic acid can be improved by use of particular crystalline forms. Accordingly, there is a need for various new crystalline forms of (S)-4-((2-methoxyethyl)(4-(5,6,7,8-tetrahydro-1,8-naphthyridin-2-yl)butyl)amino)-2-(quinazolin-4-ylamino)butanoic acid with different chemical and physical stabilities, and compositions and uses of the same.

BRIEF SUMMARY

In one aspect, provided herein is a crystalline form of a salt of (S)-4-((2-methoxyethyl)(4-(5,6,7,8-tetrahydro-1,8-naphthyridin-2-yl)butyl)amino)-2-(quinazolin-4-ylamino) butanoic acid or a solvate thereof, as detailed herein.

In another aspect, provided herein is a method of preparing a crystalline form of a salt of (S)-4-((2-methoxyethyl) (4-(5,6,7,8-tetrahydro-1,8-naphthyridin-2-yl)butyl)amino)-2-(quinazolin-4-ylamino)butanoic acid or a solvate thereof, as detailed herein.

In another aspect, provided herein is a composition comprising a crystalline form of a salt of (S)-4-((2-methoxyethyl)(4-(5,6,7,8-tetrahydro-1,8-naphthyridin-2-yl)butyl) amino)-2-(quinazolin-4-ylamino)butanoic acid or a solvate thereof, as detailed herein.

In another aspect, provided herein is a kit comprising a crystalline form of a salt of (S)-4-((2-methoxyethyl)(4-(5,6,7,8-tetrahydro-1,8-naphthyridin-2-yl)butyl)amino)-2-(quinazolin-4-ylamino)butanoic acid or a solvate thereof, as detailed herein.

In another aspect, provided herein is a method of treating a fibrotic disease in an individual (such as a human) in need thereof comprising administering to the individual a therapeutically effective amount of a crystalline form or a composition disclosed herein. In some embodiments, the fibrotic disease is pulmonary fibrosis (such as IPF), liver fibrosis, skin fibrosis, scleroderma, cardiac fibrosis, renal fibrosis, gastrointestinal fibrosis, primary sclerosing cholangitis, or biliary fibrosis (such as PBC).

In another aspect, provided is a method of delaying the onset and/or development of a fibrotic disease in an individual (such as a human) who is at risk for developing a fibrotic disease comprising administering to the individual a therapeutically effective amount of a crystalline form or a composition disclosed herein. In some embodiments, the fibrotic disease is pulmonary fibrosis (such as IPF), liver fibrosis, skin fibrosis, scleroderma, cardiac fibrosis, renal fibrosis, gastrointestinal fibrosis, primary sclerosing cholangitis, or PBC. In some embodiments, the individual at risk of developing a fibrotic disease has or is suspected of having NAFLD, NASH, CKD, scleroderma, Crohn's Disease, NSIP, PSC, PBC, or is an individual who has had or is suspected of having had a myocardial infarction.

Also provided is a crystalline form or a composition for use in the treatment of a fibrotic disease. Also provided is use of a crystalline form or a composition for use in the treatment of a fibrotic disease. Also provided is use of a crystalline form or a composition for use in the manufacture of a medicament for the treatment of a fibrotic disease.

DETAILED DESCRIPTION

Definitions

Figure 1A:
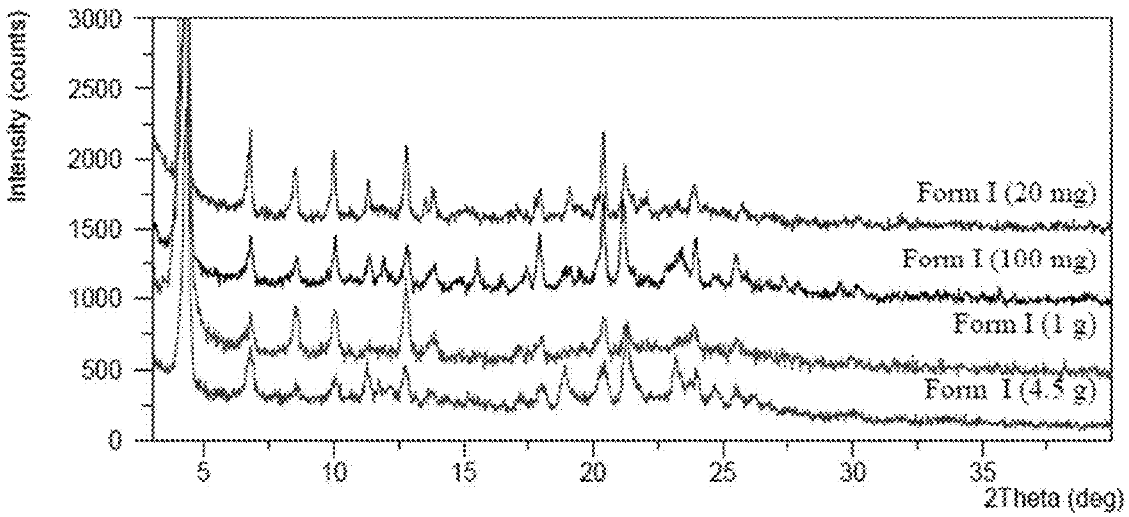
FIG. 1A shows experimental X-ray powder diffraction (XRPD) patterns of a crystalline form of a phosphate salt of (S)-4-((2-methoxyethyl)(4-(5,6,7,8-tetrahydro-1,8-naphthyridin-2-yl)butyl)amino)-2-(quinazolin-4-ylamino)butanoic acid (Form I) (from top to bottom: Form I prepared on 20 mg scale, Form I prepared on 100 mg scale, Form I prepared on 1 g scale, Form I prepared on 4.5 g scale).

As used herein, unless clearly indicated otherwise, use of the terms "a", "an" and the like refers to one or more.

As used herein, reference to "about" a value or parameter herein includes (and describes) embodiments that are directed to that value or parameter per se. For example, description referring to "about X" includes description of "X". As used herein, and unless otherwise specified, the terms "about" and "approximately," when used in connection with doses, amounts, or weight percent of ingredients of a composition or a dosage form, mean a dose, amount, or weight percent that is recognized by those of ordinary skill in the art to provide a pharmacological effect equivalent to that obtained from the specified dose, amount, or weight percent. Specifically, the terms "about" and "approximately," when used in this context, contemplate a dose, amount, or weight percent within 20%, within 15%, within 10%, within 5%, within 4%, within 3%, within 2%, within 1%, or within 0.5% of the specified dose, amount, or weight percent.

As used herein, the term "crystalline form" refers to a crystalline solid form of a chemical compound, including, but not limited to, a single-component or multiple-component crystal form, e.g., a polymorph of a compound; or a solvate, a hydrate, a clathrate, a cocrystal, a salt of a compound, or a polymorph thereof. The term "crystal forms" and related terms herein refers to the various crystalline modifications of a given substance, including, but not limited to, polymorphs, solvates, hydrates, co-crystals and other molecular complexes, as well as salts, solvates of salts, hydrates of salts, other molecular complexes of salts, and polymorphs thereof. Crystal forms of a substance can be obtained by a number of methods, as known in the art. Such methods include, but are not limited to, melt recrystallization, melt cooling, solvent recrystallization, slurrying, recrystallization in confined spaces such as, e.g., in nanopores or capillaries, recrystallization on surfaces or templates such as, e.g., on polymers, recrystallization in the presence of additives, such as, e.g., anti-solvents, co-crystal counter-molecules, desolvation, dehydration, rapid evaporation, rapid cooling, slow cooling, vapor diffusion, sublimation, grinding and solvent-drop grinding.

As used herein, "solvate" encompasses solvates, partial solvates, and channel solvates. As such, a solvate need not contain an exact stoichiometric ratio of compound:solvent, but may include ratios of compound:solvent permitted by experimental variance. The term "solvate" is further intended to include aqueous and non-aqueous solvated forms (e.g., hydrates, ethanolates, etc.). Thus, it is understood that a solvate encompasses stoichiometric solvates, channel solvates and partial solvates. It is also understood that a hydrate encompasses stoichiometric hydrates, channel hydrates and partial hydrates. An exemplary solvate of a phosphate salt is a channel hydrate.

Unless clearly indicated otherwise, "an individual" as used herein intends a mammal, including but not limited to a primate, human, bovine, horse, feline, canine, or rodent. In one variation, the individual is a human.

As used herein, "treatment" or "treating" is an approach for obtaining beneficial or desired results including clinical results. Beneficial or desired results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, delaying the occurrence or recurrence of the disease, delay or slowing the progression of the disease, ameliorating the disease state, providing a remission (whether partial or total) of the disease, decreasing the dose of one or more other medications required to treat the disease, enhancing effect of another medication, delaying the progression of the disease, increasing the quality of life, and/or prolonging survival. Also encompassed by "treatment" is a reduction of pathological consequence of fibrosis. The methods of the invention contemplate any one or more of these aspects of treatment.

As used herein, the term "effective amount" intends such amount of a compound of the invention which should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents (e.g., a compound, or pharmaceutically acceptable salt thereof), and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

As used herein, a "therapeutically effective amount" refers to an amount of a compound or salt thereof sufficient to produce a desired therapeutic outcome.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, the term "controlled release" refers to a drug-containing formulation or fraction thereof in which release of the drug is not immediate, i.e., with a "controlled release" formulation, administration does not result in immediate release of the drug into an absorption pool. The term encompasses depot formulations designed to gradually release the drug compound over an extended period of time. Controlled release formulations can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

Unless otherwise stated, "substantially pure" intends a composition that contains no more than about 10% impurity, such as a composition comprising less than about 9%, about 7%, about 5%, about 3%, about 1%, or about 0.5% impurity.

It is understood that aspects and embodiments described herein as "comprising" include "consisting of" and "consisting essentially of" embodiments.

As used herein, the term "substantially as shown in" when referring, for example, to an XRPD pattern, a DSC graph, a TGA graph, or a GVS graph, includes a pattern or graph that is not necessarily identical to those depicted herein, but that falls within the limits of experimental error or deviations when considered by one of ordinary skill in the art.

Crystalline Forms

In one aspect, provided herein is a crystalline form of a salt of (S)-4-((2-methoxyethyl)(4-(5,6,7,8-tetrahydro-1,8-naphthyridin-2-yl)butyl)amino)-2-(quinazolin-4-ylamino) butanoic acid, a compound having the structure shown below, or a solvate thereof.

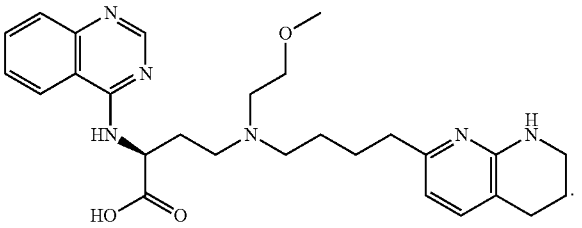 [SMILES: COCCN(CCCCc1ccc2c(n1)NCCC2)CC[C@H](Nc1ncnc2ccccc12)C(=O)O]

As used herein, a reference to the "parent compound" means the salt-free form of S)-4-((2-methoxyethyl)(4-(5,6,7,8-tetrahydro-1,8-naphthyridin-2-yl)butyl)amino)-2-(quinazolin-4-ylamino)butanoic acid. Likewise, reference to "(S)-4-((2-methoxyethyl)(4-(5,6,7,8-tetrahydro-1,8-naphthyridin-2-yl) butyl)amino)-2-(quinazolin-4-ylamino)butanoic acid" alone or its structural formula alone will, unless otherwise noted or made clear in the context in which the reference is used, be a reference to the parent compound.

The crystalline forms disclosed herein may provide the advantages of bioavailability and stability and may be suitable for use as an active agent in a pharmaceutical composition. Variations in the crystal structure of a pharmaceutical drug substance may affect the dissolution rate (which may affect bioavailability, etc.), manufacturability (e.g., ease of handling, ease of purification, ability to consistently prepare doses of known strength, etc.) and stability (e.g., thermal stability, shelf life (including resistance to degradation), etc.) of a pharmaceutical drug product. Such variations may affect the methods of preparation or formulation of pharmaceutical compositions in different dosage or delivery forms, such as solid oral dosage forms including tablets and capsules. Compared to other forms such as non-crystalline or amorphous forms, crystalline forms may provide desired or suitable hygroscopicity, particle size control, dissolution rate, solubility, purity, physical and chemical stability, manufacturability, yield, reproducibility, and/or process control. Thus, the crystalline forms disclosed herein may provide advantages of improving the manufacturing process of an active agent or the stability or storability of a drug product form of the active agent, or having suitable bioavailability and/or stability as an active agent.

Crystalline Form of Phosphate Salt

In some embodiments, provided herein is a crystalline form of a phosphate salt of (S)-4-((2-methoxyethyl)(4-(5,6,7,8-tetrahydro-1,8-naphthyridin-2-yl)butyl)amino)-2-(quinazolin-4-ylamino)butanoic acid (Form I).

In some embodiments, Form I has an XRPD pattern substantially as shown in FIG. 1A. Positions of peaks and relative peak intensities that may be observed for the crystalline form using XRPD are shown in Table 1.

TABLE 1

| Pos. [°2θ] | Height [cts] | Rel. Int. [%] | d-spacing [Å] |
|---|---|---|---|
| 4.31 | 1297.58 | 100 | 20.52 |
| 6.76 | 230.64 | 17.77 | 13.07 |
| 8.55 | 50.37 | 3.88 | 10.35 |
| 10.04 | 102.63 | 7.91 | 8.81 |
| 11.25 | 184.73 | 14.24 | 7.86 |
| 12.75 | 163.96 | 12.64 | 6.94 |
| 13.76 | 51.31 | 3.95 | 6.44 |
| 17.20 | 37.64 | 2.90 | 5.16 |
| 18.02 | 88.31 | 6.81 | 4.92 |
| 18.89 | 194.44 | 14.99 | 4.70 |
| 20.38 | 188.34 | 14.51 | 4.36 |
| 21.29 | 416.36 | 32.09 | 4.17 |
| 23.16 | 227.05 | 17.50 | 3.84 |
| 23.97 | 172.01 | 13.26 | 3.71 |
| 24.68 | 112.48 | 8.67 | 3.61 |
| 25.50 | 96.45 | 7.43 | 3.49 |
| 26.18 | 69.28 | 5.34 | 3.40 |
| 29.88 | 24.52 | 1.89 | 2.99 |
| 33.49 | 15.54 | 1.20 | 2.68 |

In some embodiments, Form I has an XRPD pattern comprising peaks provided in Table 1. In some embodiments, Form I has an XRPD pattern comprising one or more (e.g., at least one, at least two, at least three, at least four, at least five, at least six, at least seven, at least eight, at least nine, or at least ten) of the peaks at angles 2-theta with the greatest intensity in the XRPD pattern substantially as shown in FIG. 1A, or as provided in Table 1. It should be understood that relative intensities and peak assignments can vary depending on a number of factors, including sample preparation, mounting, the instrument and analytical procedure and settings used to obtain the spectrum, temperature effects on the unit cell, and extent of solvation, e.g., hydration, of the sample. For example, relative peak intensities and peak assignments can vary within experimental error. In some embodiments, each peak assignment listed herein, including for Form I, can independently vary by ±0.6 degrees, ±0.4 degrees, ±0.2 degrees, or ±0.1 degrees 2-theta. In some embodiments, each peak assignment listed herein, including for Form I, can independently vary by ±0.2 degrees 2-theta.

In some embodiments, Form I has an XRPD pattern comprising peaks as assigned at angles 2-theta in degrees as recited in Table 1, each peak of which can independently vary in assignment at angle 2-theta in degrees as described herein. For example, Form I may have an XRPD pattern comprising peaks each assigned at an angle 2-theta in degrees of about 4.31 (e.g., 4.31±0.2), about 6.76 (e.g., 6.76±0.2), about 8.55 (e.g., 8.55±0.2), about 10.04 (e.g., 10.04±0.2), about 11.25 (e.g., 11.25±0.2), about 12.75 (e.g., 12.75±0.2), about 13.76 (e.g., 13.76±0.2), about 17.20 (e.g., 17.20±0.2), about 18.02 (e.g., 18.02±0.2), about 18.89 (e.g., 18.89±0.2), about 20.38 (e.g., 20.38±0.2), about 21.29 (e.g., 21.29±0.2), about 23.16 (e.g., 23.16±0.2), about 23.97 (e.g., 23.97±0.2), about 24.68 (e.g., 24.68±0.2), about 25.50 (e.g., 25.50±0.2), about 26.18 (e.g., 26.18±0.2), about 29.88 (e.g., 29.88±0.2), and about 33.49 (e.g., 33.49±0.2). In some embodiments, Form I has an XRPD pattern comprising one or more (e.g., at least one, at least two, at least three, at least four, at least five, at least six, at least seven, at least eight, at least nine, or at least ten) peaks each assigned at angles 2-theta in degrees of about: 4.31 (e.g., 4.31±0.2), about 6.76

(e.g., 6.76±0.2), about 8.55 (e.g., 8.55±0.2), about 10.04 (e.g., 10.04±0.2), about 11.25 (e.g., 11.25±0.2), about 12.75 (e.g., 12.75±0.2), about 13.76 (e.g., 13.76±0.2), about 17.20 (e.g., 17.20±0.2), about 18.02 (e.g., 18.02±0.2), about 18.89 (e.g., 18.89±0.2), about 20.38 (e.g., 20.38±0.2), about 21.29 (e.g., 21.29±0.2), about 23.16 (e.g., 23.16±0.2), about 23.97 (e.g., 23.97±0.2), about 24.68 (e.g., 24.68±0.2), about 25.50 (e.g., 25.50±0.2), about 26.18 (e.g., 26.18±0.2), about 29.88 (e.g., 29.88±0.2), and about 33.49 (e.g., 33.49±0.2). In some embodiments, Form I has an XRPD pattern comprising peaks each assigned at angles 2-theta in degrees of about 4.31 (e.g., 4.31±0.2), about 6.76 (e.g., 6.76±0.2), about 11.25 (e.g., 11.25±0.2), about 12.75 (e.g., 12.75±0.2), about 18.89 (e.g., 18.89±0.2), about 20.38 (e.g., 20.38±0.2), about 21.29 (e.g., 21.29±0.2), about 23.16 (e.g., 23.16±0.2), about 23.97 (e.g., 23.97±0.2), and about 24.68 (e.g., 24.68±0.2). In some embodiments, Form I has an XRPD pattern comprising one or more (e.g., at least one, at least two, at least three, at least four, at least five, at least six, at least seven, at least eight, at least nine, or at least ten) peaks each assigned at angles 2-theta in degrees of about 4.31 (e.g., 4.31±0.2), about 6.76 (e.g., 6.76±0.2), about 11.25 (e.g., 11.25±0.2), about 12.75 (e.g., 12.75±0.2), about 18.89 (e.g., 18.89±0.2), about 20.38 (e.g., 20.38±0.2), about 21.29 (e.g., 21.29±0.2), about 23.16 (e.g., 23.16±0.2), about 23.97 (e.g., 23.97±0.2), and about 24.68 (e.g., 24.68±0.2). In some embodiments, Form I has an XRPD pattern comprising peaks each assigned at angles 2-theta in degrees of about: 4.31 (e.g., 4.31±0.2), about 6.76 (e.g., 6.76±0.2), about 18.89 (e.g., 18.89±0.2), about 21.29 (e.g., 21.29±0.2), and about 23.16 (e.g., 23.16±0.2). In some embodiments, Form I has an XRPD pattern comprising one or more (e.g., at least one, at least two, at least three, at least four, or at least five) peaks each assigned at angles 2-theta in degrees of about 4.31 (e.g., 4.31±0.2), about 6.76 (e.g., 6.76±0.2), about 18.89 (e.g., 18.89±0.2), about 21.29 (e.g., 21.29±0.2), and about 23.16 (e.g., 23.16±0.2). In some embodiments, Form I has an XRPD pattern comprising peaks assigned at angles 2-theta in degrees of about 4.31, about 6.76, about 18.89, about 21.29, and about 23.16. In some embodiments, Form I has an XRPD pattern comprising peaks assigned at angles 2-theta in degrees of about 4.31±0.2, about 6.76±0.2, about 18.89±0.2, about 21.29±0.2, and about 23.16±0.2. In some embodiments, Form I has an XRPD pattern comprising peaks assigned at angles 2-theta in degrees of about 4.31, about 6.76, about 11.25, and about 12.75. In some embodiments, Form I has an XRPD pattern comprising peaks assigned at angles 2-theta in degrees of about 4.31±0.2, about 6.76±0.2, about 11.25±0.2, and about 12.75±0.2. In some embodiments, Form I has an XRPD pattern comprising peaks assigned at angles 2-theta in degrees of about 4.31, about 6.76, and about 11.25. In some embodiments, Form I has an XRPD pattern comprising peaks assigned at angles 2-theta in degrees of about 4.31±0.2, about 6.76±0.2, and about 11.25±0.2. In some embodiments, Form I has an XRPD pattern comprising peaks assigned at angles 2-theta in degrees of about 4.31, about 6.76, and about 12.75. In some embodiments, Form I has an XRPD pattern comprising peaks assigned at angles 2-theta in degrees of about 4.31±0.2, about 6.76±0.2, and about 12.75±0.2. In some embodiments, Form I has an XRPD pattern comprising peaks assigned at angles 2-theta in degrees of about 4.31, and about 6.76. In some embodiments, Form I has an XRPD pattern comprising peaks assigned at angles 2-theta in degrees of about 4.31±0.2, and about 6.76±0.2. In some embodiments, Form I has an XRPD pattern comprising a peak assigned at an angle 2-theta in degrees of about 4.31. In some embodiments, Form I has an XRPD pattern comprising a peak assigned at an angle 2-theta in degrees of about 4.31±0.2.

Figure 1B:
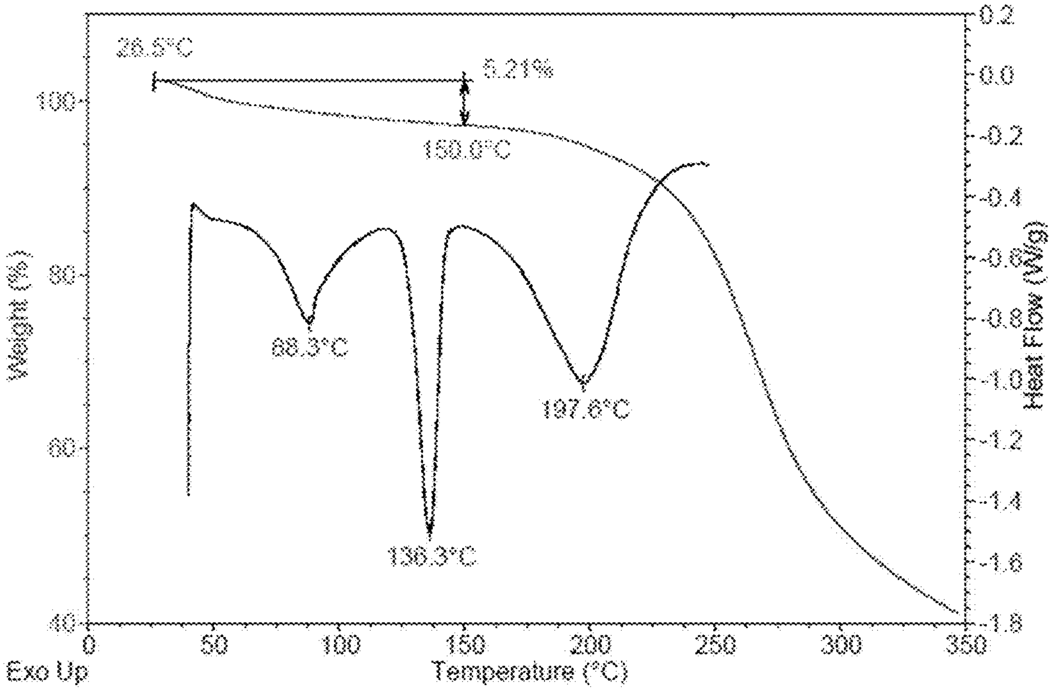
FIG. 1B shows differential scanning calorimetry (DSC) and thermogravimetric analysis (TGA) graphs of Form I prepared on 20 mg scale.
Figure 1C:
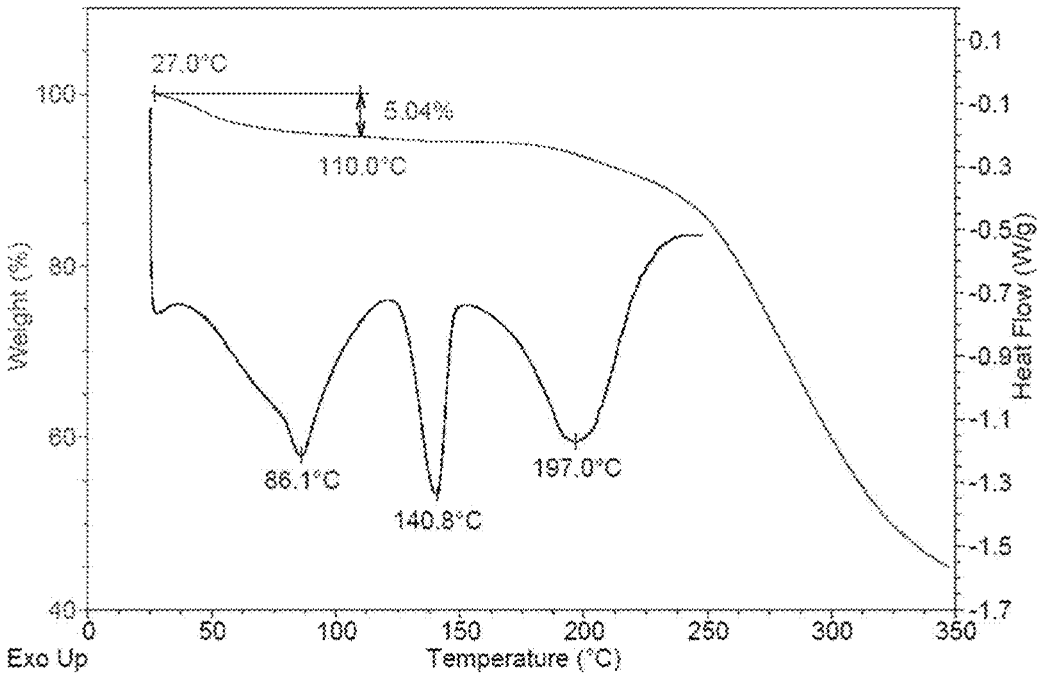
FIG. 1C shows DSC and TGA graphs of Form I prepared on 100 mg scale.
Figure 1D:
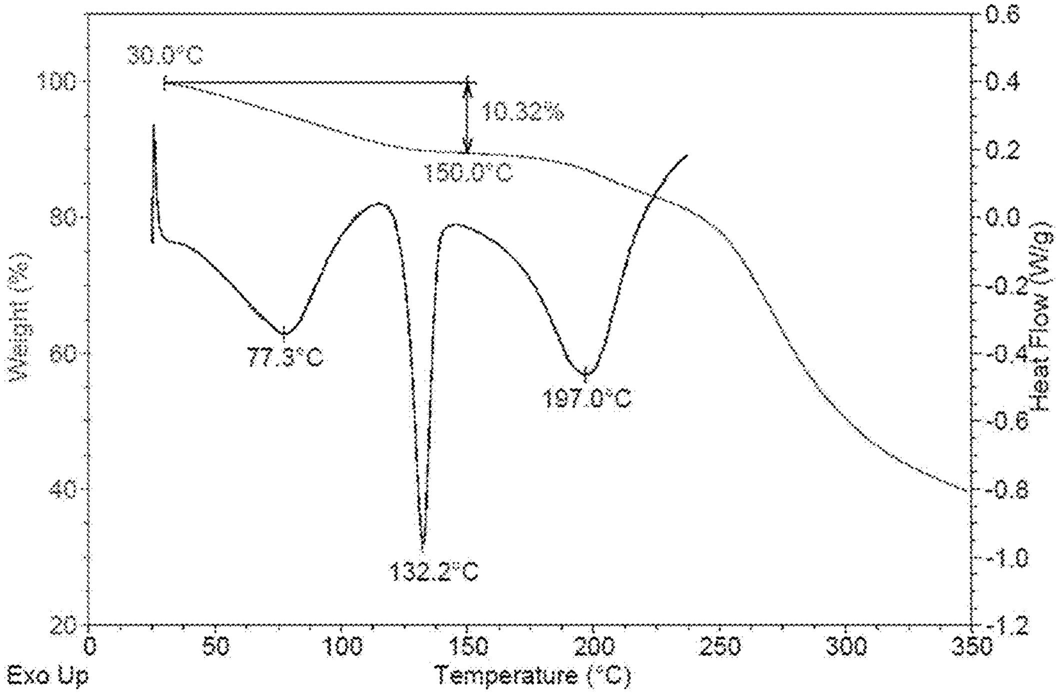
FIG. 1D shows DSC and TGA graphs of Form I prepared on 1 g scale.
Figure 1E:
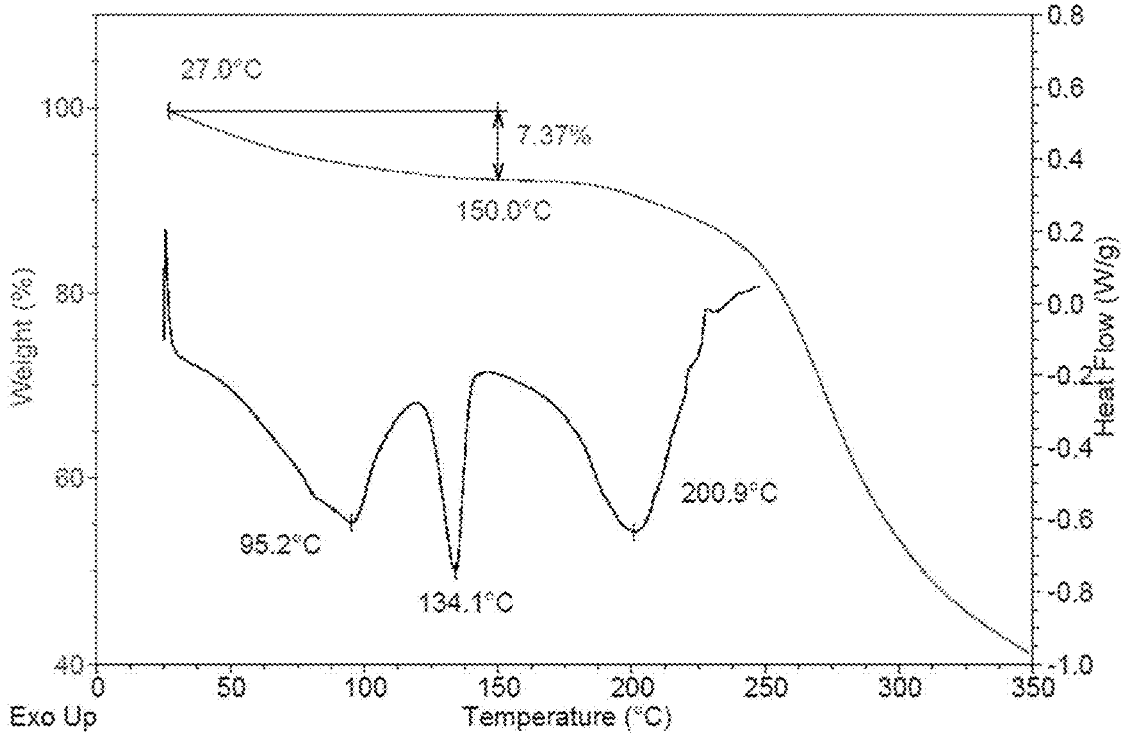
FIG. 1E shows DSC and TGA graphs of Form I prepared on 4.5 g scale.

In some embodiments, Form I has a DSC graph substantially as shown in FIG. 1B, FIG. 1C, FIG. 1D, or FIG. 1E. In some embodiments, Form I has a DSC graph substantially as shown in FIG. 1B. In some embodiments, Form I is characterized as having endotherm peaks at about 88.3° C., 136.3° C., and/or about 197.6° C., as determined by DSC. In some embodiments, Form I has a DSC graph substantially as shown in FIG. 1C. In some embodiments, Form I is characterized as having endotherm peaks at about 86.1° C., about 140.8° C., and/or about 197.0° C., as determined by DSC. In some embodiments, Form I has a DSC graph substantially as shown in FIG. 1D. In some embodiments, Form I is characterized as having endotherm peaks at about 77.3° C., 132.2° C., and/or about 197.0° C., as determined by DSC. In some embodiments, Form I has a DSC graph substantially as shown in FIG. 1E. In some embodiments, Form I is characterized as having endotherm peaks at about 95.2° C., about 134.1° C., and/or about 200.9° C., as determined by DSC.

In some embodiments, Form I has a TGA graph substantially as shown in FIG. 1B, FIG. 1C, FIG. 1D, or FIG. 1E. In some embodiments, Form I has a TGA graph substantially as shown in FIG. 1B. In some embodiments, Form I is characterized as showing a weight loss of about 5.21% after heating from about 26.5° C. to about 150.0° C., as determined by TGA. In some embodiments, Form I has a TGA graph substantially as shown in FIG. 1C. In some embodiments, Form I is characterized as showing a weight loss of about 5.04% after heating from about 27.0° C. to about 110.0° C., as determined by TGA. In some embodiments, Form I has a TGA graph substantially as shown in FIG. 1D. In some embodiments, Form I is characterized as showing a weight loss of about 10.32% after heating from about 30.0° C. to about 150.0° C., as determined by TGA. In some embodiments, Form I has a TGA graph substantially as shown in FIG. 1E. In some embodiments, Form I is characterized as showing a weight loss of about 7.37% after heating from about 27.0° C. to about 150.0° C., as determined by TGA.

Figure 1F:
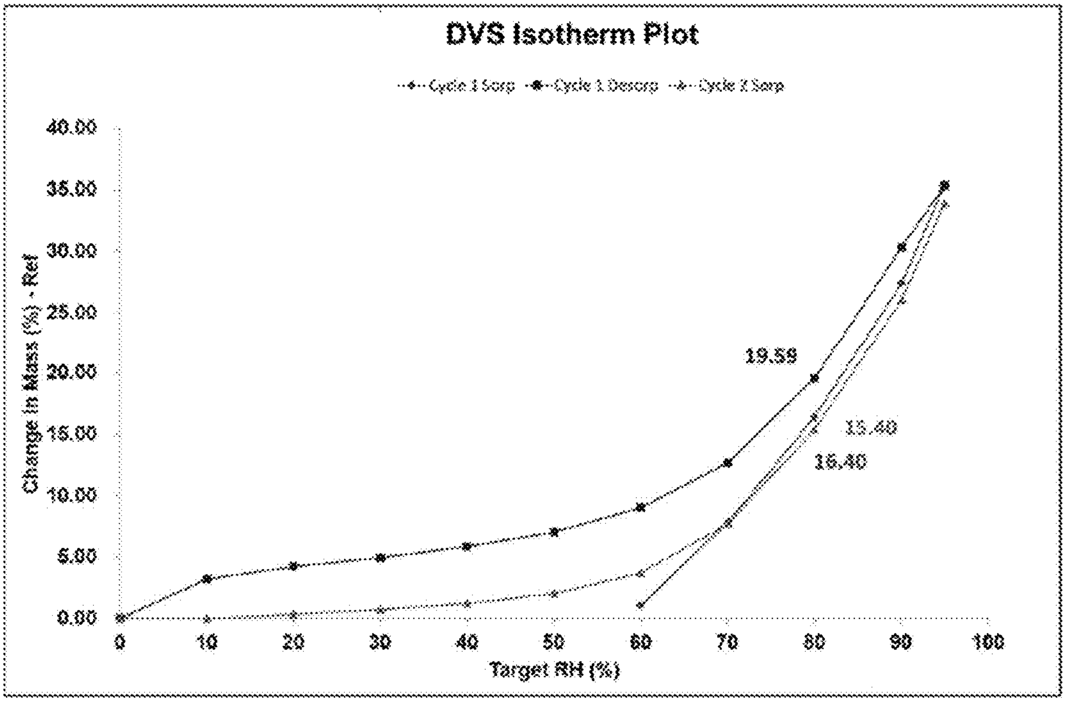
FIG. 1F shows a Dynamic Vapor Sorption (DVS) graph of Form I prepared on 4.5 g scale.

In some embodiments, Form I has a DVS graph substantially as shown in FIG. 1F.

In some embodiments of Form I, at least one, at least two, at least three, at least four, at least five, at least six, or all of the following (a)-(g) apply:

(a) Form I has an XRPD pattern comprising
  (i) peaks at angles 2-theta of about 4.31 (e.g., 4.31±0.2), about 6.76 (e.g., 6.76±0.2), about 18.89 (e.g., 18.89±0.2), about 21.29 (e.g., 21.29±0.2), and about 23.16 (e.g., 23.16±0.2) degrees,
  (ii) peaks at angles 2-theta of about 4.31 (e.g., 4.31±0.2), about 6.76 (e.g., 6.76±0.2), about 11.25 (e.g., 11.25±0.2), about 12.75 (e.g., 12.75±0.2), about 18.89 (e.g., 18.89±0.2), about 20.38 (e.g., 20.38±0.2), about 21.29 (e.g., 21.29±0.2), about 23.16 (e.g., 23.16±0.2), about 23.97 (e.g., 23.97±0.2), and about 24.68 (e.g., 24.68±0.2) degrees, or
  (iii) peaks at angles 2-theta of about 4.31 (e.g., 4.31±0.2), about 6.76 (e.g., 6.76±0.2), about 8.55 (e.g., 8.55±0.2), about 10.04 (e.g., 10.04±0.2), about 11.25 (e.g., 11.25±0.2), about 12.75 (e.g., 12.75±0.2), about 13.76 (e.g., 13.76±0.2), about 17.20 (e.g., 17.20±0.2), about 18.02 (e.g., 18.02±0.2), about 18.89 (e.g., 18.89±0.2), about 20.38 (e.g., 20.38±0.2), about 21.29 (e.g., 21.29±0.2), about 23.16 (e.g., 23.16±0.2), about 23.97 (e.g., 23.97±0.2), about 24.68 (e.g., 24.68±0.2), about 25.50 (e.g., 25.50±0.2), about 26.18 (e.g., 26.18±0.2), about 29.88 (e.g., 29.88±0.2), and about 33.49 (e.g., 33.49±0.2) degrees;

(b) Form I has an XRPD pattern substantially as shown in FIG. 1A;

(c) Form I has a DSC graph substantially as shown in FIG. 1B, FIG. 1C, FIG. 1D, or FIG. 1E;

(d) Form I is characterized as having endotherm peaks at about 88.3° C., about 136.3° C., and/or about 197.6° C., as determined by DSC; endotherm peaks at about 86.1° C., about 140.8° C., and/or about 197.0° C., as determined by DSC; endotherm peaks at about 77.3° C., 132.2° C., and/or about 197.0° C., as determined by DSC; or endotherm peaks at about 95.2° C., about 134.1° C., and/or about 200.9° C., as determined by DSC;

(e) Form I has a TGA graph substantially as shown in FIG. 1B, FIG. 1C, FIG. 1D, or FIG. 1E;

(f) Form I is characterized as showing a weight loss of about 5.21% after heating from about 26.5° C. about 150.0° C., as determined by TGA, a weight loss of about 5.04% after heating from about 27.0° C. to about 110.0° C., as determined by TGA, a weight loss of about 10.32% after heating from about 30.0° C. to about 150.0° C., as determined by TGA, or a weight loss of about 7.37% after heating from about 27.0° C. to about 150.0° C., as determined by TGA; and (g) Form I has a DVS graph substantially as shown in FIG. 1F.

Crystalline Form of Fumarate Salt

In some embodiments, provided herein is a crystalline form of a fumarate salt of (S)-4-((2-methoxyethyl)(4-(5,6,7,8-tetrahydro-1,8-naphthyridin-2-yl)butyl)amino)-2-(quinazolin-4-ylamino)butanoic acid (Form II).

Figure 2A:
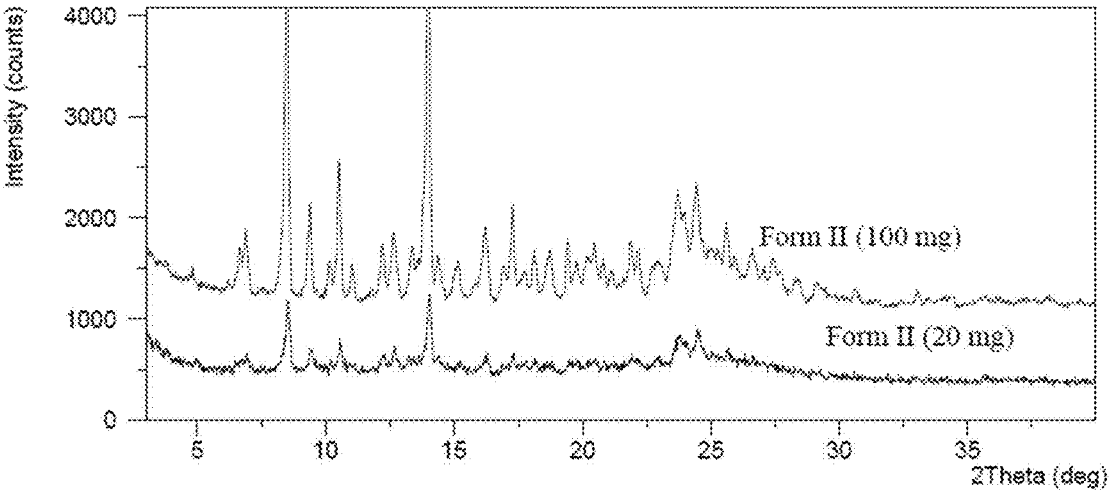
FIG. 2A shows experimental XRPD patterns of a crystalline form of a fumarate salt of (S)-4-((2-methoxyethyl) (4-(5,6,7,8-tetrahydro-1,8-naphthyridin-2-yl)butyl)amino)-2-(quinazolin-4-ylamino)butanoic acid (Form II) (top: Form II prepared on 100 mg scale; bottom: Form II prepared on 20 mg scale).

In some embodiments, Form II has an XRPD pattern substantially as shown in FIG. 2A. Positions of peaks and relative peak intensities that may be observed for the crystalline form using XRPD are shown in Table 2.

TABLE 2

| Pos. [°2θ] | Height [cts] | Rel. Int. [%] | d-spacing [Å] |
|---|---|---|---|
| 3.37 | 426.85 | 11.26 | 26.25 |
| 3.75 | 432.53 | 11.41 | 23.54 |
| 4.78 | 320.81 | 8.46 | 18.47 |
| 6.60 | 464.27 | 12.25 | 13.39 |
| 6.87 | 727.06 | 19.18 | 12.87 |
| 8.47 | 3657.05 | 96.49 | 10.44 |
| 9.37 | 997.4 | 26.32 | 9.44 |
| 10.14 | 425.61 | 11.23 | 8.72 |
| 10.51 | 1438.57 | 37.96 | 8.42 |
| 11.01 | 397.76 | 10.49 | 8.03 |
| 12.20 | 585.02 | 15.44 | 7.26 |
| 12.63 | 715.21 | 18.87 | 7.01 |
| 13.34 | 540.6 | 14.26 | 6.64 |
| 13.98 | 3790.08 | 100 | 6.34 |
| 14.37 | 467.85 | 12.34 | 6.17 |
| 15.00 | 303.65 | 8.01 | 5.91 |
| 15.14 | 418.58 | 11.04 | 5.85 |
| 16.20 | 786.22 | 20.74 | 5.47 |
| 16.92 | 374.43 | 9.88 | 5.24 |
| 17.26 | 975.64 | 25.74 | 5.14 |
| 17.73 | 330.91 | 8.73 | 5.00 |
| 18.11 | 552.94 | 14.59 | 4.90 |
| 18.72 | 567.15 | 14.96 | 4.74 |
| 19.42 | 624.59 | 16.48 | 4.57 |
| 19.75 | 404.1 | 10.66 | 4.49 |
| 20.19 | 458.69 | 12.1 | 4.40 |
| 20.46 | 599.55 | 15.82 | 4.34 |
| 20.78 | 433.01 | 11.42 | 4.27 |
| 21.12 | 338.82 | 8.94 | 4.21 |
| 21.87 | 622.11 | 16.41 | 4.06 |
| 22.15 | 529.9 | 13.98 | 4.01 |
| 22.67 | 354.25 | 9.35 | 3.92 |
| 22.96 | 408.39 | 10.78 | 3.87 |
| 23.70 | 1124.85 | 29.68 | 3.75 |
| 24.01 | 804.75 | 21.23 | 3.71 |
| 24.43 | 1209.04 | 31.9 | 3.64 |
| 25.59 | 797.16 | 21.03 | 3.48 |
| 25.92 | 444.4 | 11.73 | 3.44 |
| 26.58 | 518.74 | 13.69 | 3.35 |
| 27.06 | 319.09 | 8.42 | 3.30 |
| 27.40 | 458.04 | 12.09 | 3.26 |
| 27.66 | 332.37 | 8.77 | 3.23 |
| 28.33 | 252.28 | 6.66 | 3.15 |
| 29.13 | 202.37 | 5.34 | 3.07 |
| 29.33 | 147.36 | 3.89 | 3.05 |
| 30.62 | 160.6 | 4.24 | 2.92 |
| 31.46 | 40.41 | 1.07 | 2.84 |
| 33.03 | 131.01 | 3.46 | 2.71 |
| 33.45 | 50.06 | 1.32 | 2.68 |
| 34.35 | 67.24 | 1.77 | 2.61 |
| 35.66 | 80.42 | 2.12 | 2.52 |
| 38.15 | 55.5 | 1.46 | 2.36 |

In some embodiments, Form II has an XRPD pattern comprising peaks provided in Table 2. In some embodiments, Form II has an XRPD pattern comprising one or more (e.g., at least one, at least two, at least three, at least four, at least five, at least six, at least seven, at least eight, at least nine, or at least ten) of the peaks at angles 2-theta with the greatest intensity in the XRPD pattern substantially as shown in FIG. 2A or as provided in Table 2. It should be understood that relative intensities and peak assignments can vary depending on a number of factors, including sample preparation, mounting, the instrument and analytical procedure and settings used to obtain the spectrum, temperature effects on the unit cell, and extent of solvation, e.g., hydration, of the sample. For example, relative peak intensities and peak assignments can vary within experimental error. In some embodiments, each peak assignment listed herein, including for Form II, can independently vary by ±0.6 degrees, ±0.4 degrees, ±0.2 degrees, or ±0.1 degrees 2-theta. In some embodiments, each peak assignment listed herein, including for Form II, can independently vary by ±0.2 degrees 2-theta.

In some embodiments, Form II has an XRPD pattern comprising peaks as assigned at angles 2-theta in degrees as recited in Table 2, each peak of which can independently vary in assignment at angle 2-theta in degrees as described herein. For example, Form II may have an XRPD pattern comprising peaks each assigned at an angle 2-theta in degrees of about 6.87 (e.g., 6.87±0.2), about 8.47 (e.g., 8.47±0.2), about 9.37 (e.g., 9.37±0.2), about 10.51 (e.g., 10.51±0.2), about 12.20 (e.g., 12.20±0.2), about 12.63 (e.g., 12.63±0.2), about 13.34 (e.g., 13.34±0.2), about 13.98 (e.g., 13.98±0.2), about 16.20 (e.g., 16.20±0.2), about 17.26 (e.g., 17.26±0.2), about 18.11 (e.g., 18.11±0.2), about 18.72 (e.g., 18.72±0.2), about 19.42 (e.g., 19.42±0.2), about 20.46 (e.g., 20.46±0.2), about 21.87 (e.g., 21.87±0.2), about 22.15 (e.g., 22.15±0.2), about 23.70 (e.g., 23.70±0.2), about 24.01 (e.g., 24.01±0.2), about 24.43 (e.g., 24.43±0.2), and about 25.59 (e.g., 25.59±0.2) degrees. In some embodiments, Form II has an XRPD pattern comprising one or more (e.g., at least one, at least two, at least three, at least four, at least five, at least six, at least seven, at least eight, at least nine, or at least ten) peaks each assigned at angles 2-theta in degrees of: about 6.87 (e.g., 6.87±0.2), about 8.47 (e.g., 8.47±0.2), about 9.37 (e.g., 9.37±0.2), about 10.51 (e.g., 10.51±0.2), about 12.20 (e.g., 12.20±0.2), about 12.63 (e.g., 12.63±0.2), about 13.34 (e.g., 13.34±0.2), about 13.98 (e.g., 13.98±0.2), about 16.20 (e.g., 16.20±0.2), about 17.26 (e.g., 17.26±0.2), about 18.11 (e.g., 18.11±0.2), about 18.72 (e.g., 18.72±0.2), about 19.42 (e.g., 19.42±0.2), about 20.46 (e.g., 20.46±0.2), about 21.87 (e.g., 21.87±0.2), about 22.15 (e.g., 22.15±0.2), about 23.70 (e.g., 23.70±0.2), about 24.01 (e.g., 24.01±0.2), about 24.43 (e.g., 24.43±0.2), and about 25.59 (e.g., 25.59±0.2). In some embodiments, Form II has an XRPD pattern comprising peaks each assigned at angles 2-theta in degrees of: about 8.47 (e.g., 8.47±0.2), about 9.37 (e.g., 9.37±0.2), about 10.51 (e.g., 10.51±0.2), about 13.98 (e.g., 13.98±0.2), about 16.20 (e.g., 16.20±0.2), about 17.26 (e.g., 17.26±0.2), about 23.70 (e.g., 23.70±0.2), about 24.01 (e.g., 24.01±0.2), about 24.43 (e.g., 24.43±0.2), and about 25.59 (e.g., 25.59±0.2). In some embodiments, Form II has an XRPD pattern comprising one or more (e.g., at least one, at least two, at least three, at least four, at least five, at least six, at least seven, at least eight, at least nine, or at least ten) peaks each assigned at angles 2-theta in degrees of: about 8.47 (e.g., 8.47±0.2), about 9.37 (e.g., 9.37±0.2), about 10.51 (e.g., 10.51±0.2), about 13.98 (e.g., 13.98±0.2), about 16.20 (e.g., 16.20±0.2), about 17.26 (e.g., 17.26±0.2), about 23.70 (e.g., 23.70±0.2), about 24.01 (e.g., 24.01±0.2), about 24.43 (e.g., 24.43±0.2), and about 25.59 (e.g., 25.59±0.2). In some embodiments, Form II has an XRPD pattern comprising peaks each assigned at angles 2-theta in degrees of: about 8.47 (e.g., 8.47±0.2), about 10.51 (e.g., 10.51±0.2), about 13.98 (e.g., 13.98±0.2), about 23.70 (e.g., 23.70±0.2), and about 24.43 (e.g., 24.43±0.2). In some embodiments, Form II has an XRPD pattern comprising one or more (e.g., at least one, at least two, at least three, at least four, or at least five) peaks each assigned at angles 2-theta in degrees of: about 8.47 (e.g., 8.47±0.2), about 10.51 (e.g., 10.51±0.2), about 13.98 (e.g., 13.98±0.2), about 23.70 (e.g., 23.70±0.2), and about 24.43 (e.g., 24.43±0.2). In some embodiments, Form II has an XRPD pattern comprising peaks assigned at angles 2-theta in degrees of about 8.47, about 9.37, about 10.51, and about 13.98. In some embodiments, Form II has an XRPD pattern comprising peaks assigned at angles 2-theta in degrees of about 8.47±0.2, about 9.37±0.2, about 10.51±0.2, and about 13.98±0.2. In some embodiments, Form II has an XRPD pattern comprising peaks assigned at angles 2-theta in degrees of about 8.47, about 9.37, and about 10.51. In some embodiments, Form II has an XRPD pattern comprising peaks assigned at angles 2-theta in degrees of about 8.47±0.2, about 9.37±0.2, and about 10.51±0.2. In some embodiments, Form II has an XRPD pattern comprising peaks assigned at angles 2-theta in degrees of about 8.47, about 9.37, and about 13.98. In some embodiments, Form II has an XRPD pattern comprising peaks assigned at angles 2-theta in degrees of about 8.47±0.2, about 9.37±0.2, and about 13.98±0.2. In some embodiments, Form II has an XRPD pattern comprising peaks assigned at angles 2-theta in degrees of about 8.47 and about 9.37. In some embodiments, Form II has an XRPD pattern comprising peaks assigned at angles 2-theta in degrees of about 8.47±0.2 and about 9.37±0.2. In some embodiments, Form II has an XRPD pattern comprising a peak assigned at an angle 2-theta in degrees of about 8.47. In some embodiments, Form II has an XRPD pattern comprising a peak assigned at an angle 2-theta in degrees of about 8.47±0.2.

Figure 2B:
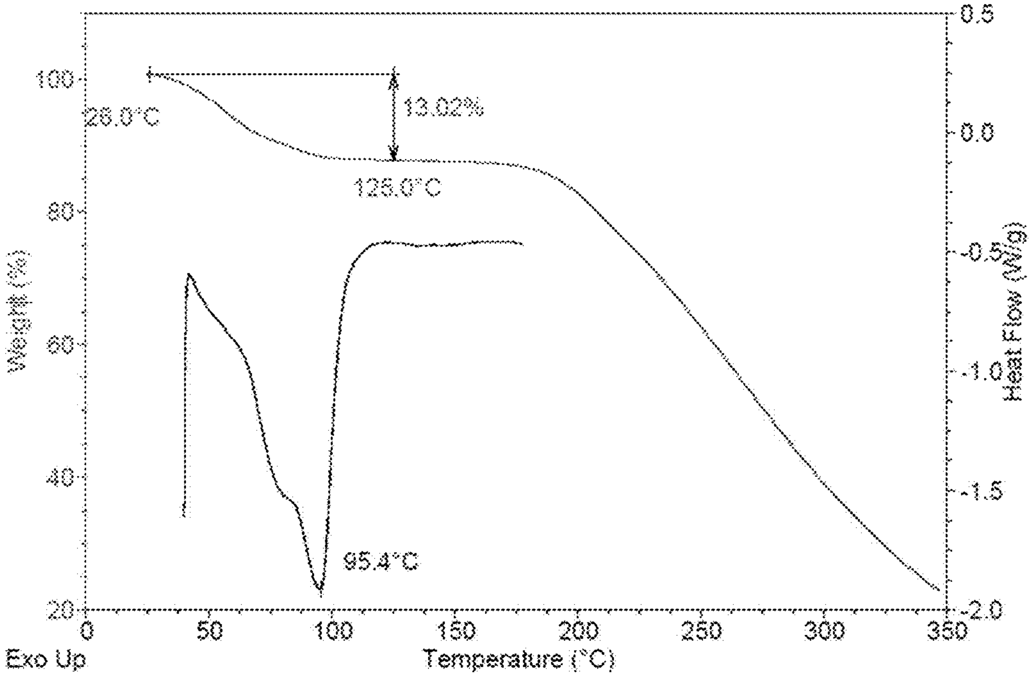
FIG. 2B shows DSC and TGA graphs of Form II prepared on 100 mg scale.

In some embodiments, Form II has a DSC graph substantially as shown in FIG. 2B. In some embodiments, Form II is characterized as having an endotherm peak at about 95.4° C.

In some embodiments, Form II has a TGA graph substantially as shown in FIG. 2B. In some embodiments, Form II is characterized as showing a weight loss of about 13.02% after heating from about 26.0° C. to about 125.0° C., as determined by TGA.

In some embodiments of Form II, at least one, at least two, at least three, at least four, at least five, or all of the following (a)-(f) apply:

(a) Form II has an XRPD pattern comprising
  (i) peaks at angles 2-theta of about 8.47 (e.g., 8.47±0.2), about 10.51 (e.g., 10.51±0.2), about 13.98 (e.g., 13.98±0.2), about 23.70 (e.g., 23.70±0.2), and about 24.43 (e.g., 24.43±0.2) degrees,
  (ii) peaks at angles 2-theta of about 8.47 (e.g., 8.47±0.2), about 9.37 (e.g., 9.37±0.2), about 10.51 (e.g., 10.51±0.2), about 13.98 (e.g., 13.98±0.2), about 16.20 (e.g., 16.20±0.2), about 17.26 (e.g., 17.26±0.2), about 23.70 (e.g., 23.70±0.2), about 24.01 (e.g., 24.01±0.2), about 24.43 (e.g., 24.43±0.2), and about 25.59 (e.g., 25.59±0.2) degrees, or
  (iii) peaks at angles 2-theta of about 6.87 (e.g., 6.87±0.2), about 8.47 (e.g., 8.47±0.2), about 9.37 (e.g., 9.37±0.2), about 10.51 (e.g., 10.51±0.2), about 12.20 (e.g., 12.20±0.2), about 12.63 (e.g., 12.63±0.2), about 13.34 (e.g., 13.34±0.2), about 13.98 (e.g., 13.98±0.2), about 16.20 (e.g., 16.20±0.2), about 17.26 (e.g., 17.26±0.2), about 18.11 (e.g., 18.11±0.2), about 18.72 (e.g., 18.72±0.2), about 19.42 (e.g., 19.42±0.2), about 20.46 (e.g., 20.46±0.2), about 21.87 (e.g., 21.87±0.2), about 22.15 (e.g., 22.15±0.2), about 23.70 (e.g., 23.70±0.2), about 24.01 (e.g., 24.01±0.2), about 24.43 (e.g., 24.43±0.2), and about 25.59 (e.g., 25.59±0.2) degrees;

(b) Form II has an XRPD pattern substantially as shown in FIG. 2A;

(c) Form II has a DSC graph substantially as shown in FIG. 2B;

(d) Form II is characterized as having an endotherm peak at about 95.4° C., as determined by DSC;

(e) Form II has a TGA graph substantially as shown in FIG. 2B; and (f) Form II is characterized as showing a weight loss of about 13.02% after heating from about 26.0° C. to about 125.0° C., as determined by TGA.

Crystalline Form of 1,5-Naphthalenedisulfonate Salt

In some embodiments, provided herein is a crystalline form of a 1,5-naphthalenedisulfonate salt of (S)-4-((2-methoxyethyl)(4-(5,6,7,8-tetrahydro-1,8-naphthyridin-2-yl)butyl)amino)-2-(quinazolin-4-ylamino)butanoic acid (Form III).

Figure 3A:
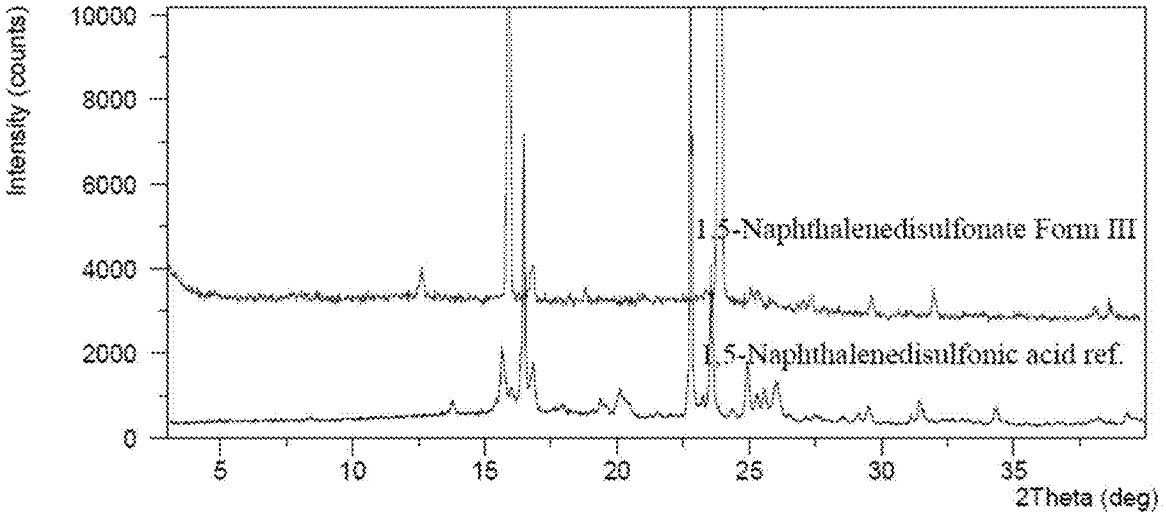
FIG. 3A shows an experimental XRPD pattern of a crystalline form of a 1,5-naphthalenedisulfonate salt of (S)-4-((2-methoxyethyl)(4-(5,6,7,8-tetrahydro-1,8-naphthyridin-2-yl)butyl)amino)-2-(quinazolin-4-ylamino)butanoic acid (Form III) (top: Form III; bottom: 1,5-naphthalenedisulfonic acid reference).

In some embodiments, Form III has an XRPD pattern substantially as shown in FIG. 3A. Positions of peaks and relative peak intensities that may be observed for the crystalline form using XRPD are shown in Table 3.

TABLE 3

| Pos. [°2θ] | Height [cts] | Rel. Int. [%] | d-spacing [Å] |
|---|---|---|---|
| 3.17 | 134.44 | 4.39 | 27.87 |
| 12.58 | 171.83 | 5.61 | 7.03 |
| 15.87 | 1829.04 | 59.71 | 5.59 |

TABLE 3-continued

| Pos. [°2θ] | Height [cts] | Rel. Int. [%] | d-spacing [Å] |
|---|---|---|---|
| 16.77 | 202.64 | 6.62 | 5.29 |
| 18.78 | 73.68 | 2.41 | 4.73 |
| 23.85 | 3063.16 | 100 | 3.73 |
| 25.30 | 73.68 | 2.41 | 3.52 |
| 27.34 | 91.67 | 2.99 | 3.26 |
| 29.61 | 122.98 | 4.01 | 3.02 |
| 31.95 | 170.25 | 5.56 | 2.80 |
| 38.05 | 52.60 | 1.72 | 2.36 |
| 38.63 | 73.12 | 2.39 | 2.33 |

In some embodiments, Form III has an XRPD pattern comprising peaks provided in Table 3. In some embodiments, Form III has an XRPD pattern comprising one or more (e.g., at least one, at least two, at least three, at least four, at least five, at least six, at least seven, at least eight, at least nine, or at least ten) of the peaks at angles 2-theta with the greatest intensity in the XRPD pattern substantially as shown in FIG. 3A or as provided in Table 3. It should be understood that relative intensities and peak assignments can vary depending on a number of factors, including sample preparation, mounting, the instrument and analytical procedure and settings used to obtain the spectrum, temperature effects on the unit cell, and extent of solvation, e.g., hydration, of the sample. For example, relative peak intensities and peak assignments can vary within experimental error. In some embodiments, each peak assignment listed herein, including for Form III, can vary by ±0.6 degrees, ±0.4 degrees, ±0.2 degrees, or ±0.1 degrees 2-theta. In some embodiments, each peak assignment listed herein, including for Form III, can independently vary by ±0.2 degrees 2-theta.

In some embodiments, Form III has an XRPD pattern comprising peaks as assigned at angles 2-theta in degrees as recited in Table 3, each peak of which can independently vary in assignment at angle 2-theta in degrees as described herein. For example, Form III may have an XRPD pattern comprising peaks each assigned at an angle 2-theta in degrees of about 3.17 (e.g., 3.17±0.2), about 12.58 (e.g., 12.58±0.2), about 15.87 (e.g., 15.87±0.2), about 16.77 (e.g., 16.77±0.2), about 18.78 (e.g., 18.78±0.2), about 23.85 (e.g., 23.85±0.2), about 25.30 (e.g., 25.30±0.2), about 27.34 (e.g., 27.34±0.2), about 29.61 (e.g., 29.61±0.2), about 31.95 (e.g., 31.95±0.2), about 38.05 (e.g., 38.05±0.2), and about 38.63 (e.g., 38.63±0.2) degrees. In some embodiments, Form III has an XRPD pattern comprising one or more (e.g., at least one, at least two, at least three, at least four, at least five, at least six, at least seven, at least eight, at least nine, or at least ten) peaks each assigned at angles 2-theta in degrees of about 3.17 (e.g., 3.17±0.2), about 12.58 (e.g., 12.58±0.2), about 15.87 (e.g., 15.87±0.2), about 16.77 (e.g., 16.77±0.2), about 18.78 (e.g., 18.78±0.2), about 23.85 (e.g., 23.85±0.2), about 25.30 (e.g., 25.30±0.2), about 27.34 (e.g., 27.34±0.2), about 29.61 (e.g., 29.61±0.2), about 31.95 (e.g., 31.95±0.2), about 38.05 (e.g., 38.05±0.2), and about 38.63 (e.g., 38.63±0.2). In some embodiments, Form III has an XRPD pattern comprising peaks each assigned at angles 2-theta in degrees of about 12.58 (e.g., 12.58±0.2), about 15.87 (e.g., 15.87±0.2), about 16.77 (e.g., 16.77±0.2), about 23.85 (e.g., 23.85±0.2), and about 31.95 (e.g., 31.95±0.2). In some embodiments, Form III has an XRPD pattern comprising one or more (e.g., at least one, at least two, at least three, at least four, or at least five) peaks each assigned at angles 2-theta in degrees of about 12.58 (e.g., 12.58±0.2), about 15.87 (e.g., 15.87±0.2), about 16.77 (e.g., 16.77±0.2), about 23.85 (e.g., 23.85±0.2), and about 31.95 (e.g., 31.95±0.2). In some embodiments, Form III has an XRPD pattern comprising peaks each assigned at angles 2-theta in degrees of about 15.87 (e.g., 15.87±0.2) and about 23.85 (e.g., 23.85±0.2). In some embodiments, Form III has an XRPD pattern comprising peaks assigned at angles 2-theta in degrees of about 12.58, about 15.87, about 16.77, and about 23.85. In some embodiments, Form III has an XRPD pattern comprising peaks assigned at angles 2-theta in degrees of about 12.58±0.2, about 15.87±0.2, about 16.77±0.2, and about 23.85±0.2. In some embodiments, Form III has an XRPD pattern comprising peaks assigned at angles 2-theta in degrees of about 12.58, about 15.87, and about 16.77. In some embodiments, Form III has an XRPD pattern comprising peaks assigned at angles 2-theta in degrees of about 12.58±0.2, about 15.87±0.2, and about 16.77±0.2. In some embodiments, Form III has an XRPD pattern comprising peaks assigned at angles 2-theta in degrees of about 12.58, about 15.87, and about 23.85. In some embodiments, Form III has an XRPD pattern comprising peaks assigned at angles 2-theta in degrees of about 12.58±0.2, about 15.87±0.2, and about 23.85±0.2. In some embodiments, Form III has an XRPD pattern comprising peaks assigned at angles 2-theta in degrees of about 12.58 and about 15.87. In some embodiments, Form III has an XRPD pattern comprising peaks assigned at angles 2-theta in degrees of about 12.58±0.2, and about 15.87±0.2. In some embodiments, Form III has an XRPD pattern comprising a peak assigned at angle 2-theta in degrees of about 12.58. In some embodiments, Form III has an XRPD pattern comprising a peak assigned at angle 2-theta in degrees of about 12.58±0.2.

Figure 3B:
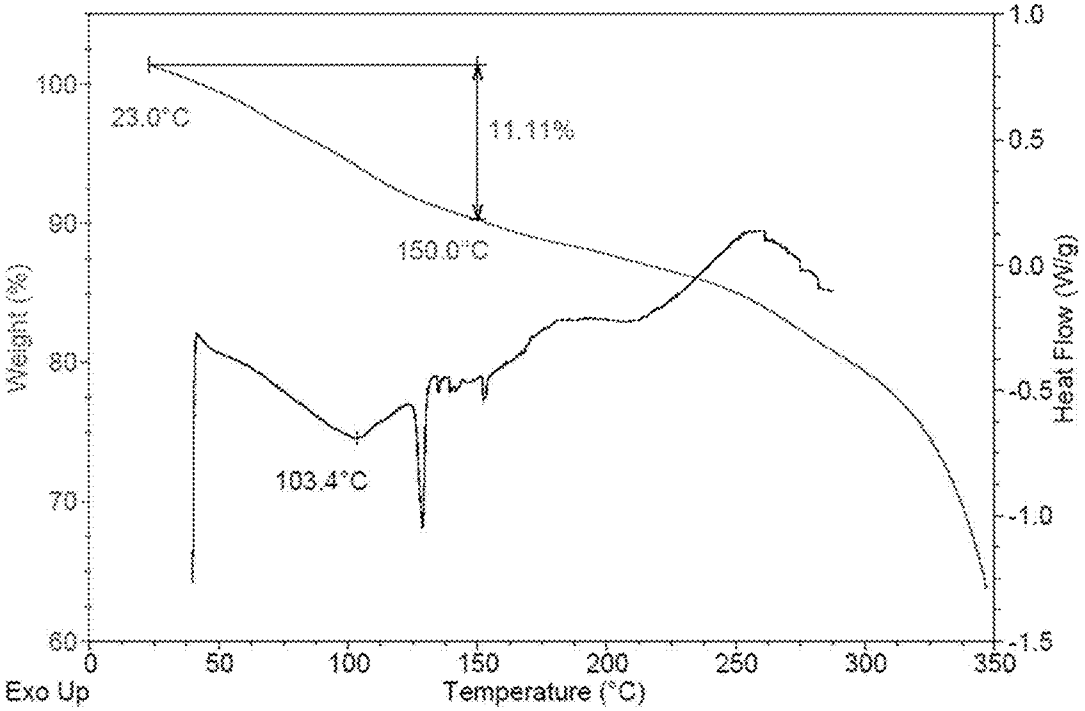
FIG. 3B shows DSC and TGA graphs of Form III.

In some embodiments, Form III has a DSC graph substantially as shown in FIG. 3B. In some embodiments, Form III is characterized as having an endotherm peak at about 103.4° C.

In some embodiments, Form III has a TGA graph substantially as shown in FIG. 3B. In some embodiments, Form III has a TGA graph substantially as shown in FIG. 1B. In some embodiments, Form III is characterized as showing a weight loss of about 11.11% after heating from about 23.0° C. to about 150.0° C., as determined by TGA.

In some embodiments of Form III, at least one, at least two, at least three, at least four, at least five, or all of the following (a)-(f) apply:

(a) Form III has an XRPD pattern comprising
  - (i) peaks at angles 2-theta of about 15.87 (e.g., 15.87±0.2) and about 23.85 (e.g., 23.85±0.2) degrees,
  - (ii) peaks at angles 2-theta of about 12.58 (e.g., 12.58±0.2), about 15.87 (e.g., 15.87±0.2), about 16.77 (e.g., 16.77±0.2), about 23.85 (e.g., 23.85±0.2), and about 31.95 (e.g., 31.95±0.2) degrees, or
  - (iii) peaks at angles 2-theta of about 3.17 (e.g., 3.17±0.2), about 12.58 (e.g., 12.58±0.2), about 15.87 (e.g., 15.87±0.2), about 16.77 (e.g., 16.77±0.2), about 18.78 (e.g., 18.78±0.2), about 23.85 (e.g., 23.85±0.2), about 25.30 (e.g., 25.30±0.2), about 27.34 (e.g., 27.34±0.2), about 29.61 (e.g., 29.61±0.2), about 31.95 (e.g., 31.95±0.2), about 38.05 (e.g., 38.05±0.2), and about 38.63 (e.g., 38.63±0.2) degrees;

(b) Form III has an XRPD pattern substantially as shown in FIG. 3A;

(c) Form III has a DSC graph substantially as shown in FIG. 3B;

(d) Form III is characterized as having an endotherm peak at about 103.4° C., as determined by DSC;

(e) Form III has a TGA graph substantially as shown in FIG. 3B; and (f) Form III is characterized as showing a weight loss of about 11.11% after heating from about 23.0° C. to about 150.0° C., as determined by TGA.

Crystalline Form of Phosphate Salt Solvate

In some embodiments, provided herein is a crystalline form of a mixed solvate of isopropyl alcohol and water of a phosphate salt of (S)-4-((2-methoxyethyl)(4-(5,6,7,8-tetrahydro-1,8-naphthyridin-2-yl)butyl)amino)-2-(quinazolin-4-ylamino)butanoic acid (Form IV).

Figure 4:
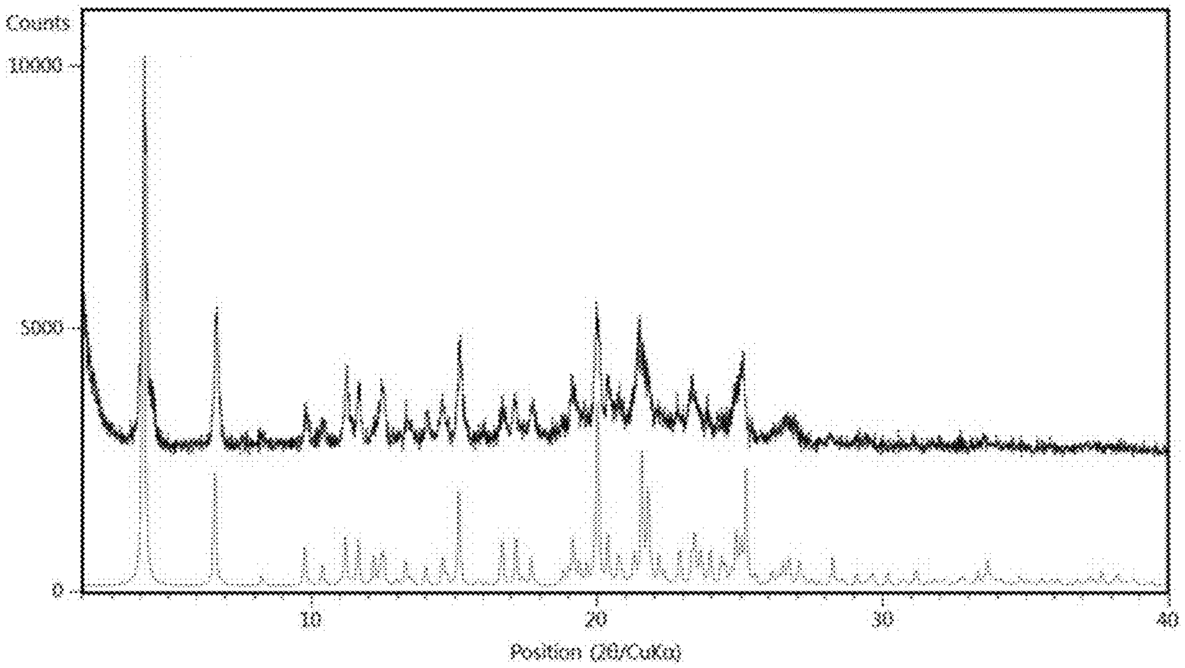
FIG. 4 shows experimental and simulated XRPD patterns of a crystalline form of a mixed solvate of isopropyl alcohol and water of a phosphate salt of (S)-4-((2-methoxyethyl)(4-(5,6,7,8-tetrahydro-1,8-naphthyridin-2-yl)butyl)amino)-2-(quinazolin-4-ylamino)butanoic acid (Form IV) (top: experimental XRPD pattern; bottom: simulated XRPD pattern).

In some embodiments, Form IV has an XRPD pattern substantially as shown in FIG. 4. Positions of peaks and relative peak intensities that may be observed for the crystalline form using XRPD are shown in Table 4.

TABLE 4*

| Pos. [°2θ] | Height [cts] | Rel. Int. [%] | d-spacing [Å] |
|---|---|---|---|
| 4.14 | 10032.59 | 100 | 21.34309 |
| 20.02 | 3193.3 | 31.83 | 4.43239 |
| 21.57 | 2307.44 | 23 | 4.11582 |
| 6.64 | 2066.06 | 20.59 | 13.29494 |
| 25.22 | 1998.24 | 19.92 | 3.52879 |
| 15.18 | 1737.53 | 17.32 | 5.83117 |
| 21.79 | 1685.86 | 16.8 | 4.07634 |
| 11.20 | 957.91 | 9.55 | 7.89512 |
| 11.65 | 943.49 | 9.4 | 7.59062 |
| 24.86 | 883.24 | 8.8 | 3.57905 |
| 17.18 | 881.6 | 8.79 | 5.15825 |
| 19.17 | 824.76 | 8.22 | 4.6259 |
| 23.42 | 824.7 | 8.22 | 3.79606 |
| 20.39 | 817.47 | 8.15 | 4.35266 |
| 16.69 | 705.83 | 7.04 | 5.3077 |
| 25.03 | 663.02 | 6.61 | 3.55525 |
| 9.78 | 656.93 | 6.55 | 9.03733 |
| 22.89 | 604.86 | 6.03 | 3.88239 |
| 23.62 | 587.8 | 5.86 | 3.7637 |
| 12.53 | 552.02 | 5.5 | 7.05696 |
| 23.96 | 527.02 | 5.25 | 3.71102 |
| 20.76 | 523.04 | 5.21 | 4.27501 |
| 14.60 | 515.46 | 5.14 | 6.06389 |
| 22.16 | 511.93 | 5.1 | 4.00832 |
| 21.31 | 500.6 | 4.99 | 4.16693 |
| 28.25 | 495.26 | 4.94 | 3.15689 |
| 17.71 | 488.53 | 4.87 | 5.00363 |
| 12.43 | 478.94 | 4.77 | 7.11454 |
| 26.72 | 473.53 | 4.72 | 3.33358 |
| 33.66 | 461.96 | 4.6 | 2.66086 |

*peaks assigned via simulation

In some embodiments, Form IV has an XRPD pattern comprising peaks provided in Table 4. In some embodiments, Form IV has an XRPD pattern comprising one or more (e.g., at least one, at least two, at least three, at least four, at least five, at least six, at least seven, at least eight, at least nine, or at least ten) of the peaks at angles 2-theta with the greatest intensity in the XRPD pattern substantially as shown in FIG. 4, or as provided in Table 4. It should be understood that relative intensities and peak assignments can vary depending on a number of factors, including sample preparation, mounting, the instrument and analytical procedure and settings used to obtain the spectrum, temperature effects on the unit cell, and extent of solvation, e.g., hydration, of the sample. For example, relative peak intensities and peak assignments can vary within experimental error. In some embodiments, each peak assignment listed herein, including for Form IV, can independently vary by ±0.6 degrees, ±0.4 degrees, ±0.2 degrees, or ±0.1 degrees 2-theta. In some embodiments, each peak assignment listed herein, including for Form IV, can independently vary by ±0.2 degrees 2-theta.

In some embodiments, Form IV has an XRPD pattern comprising peaks as assigned at angles 2-theta in degrees as recited in Table 4, each peak of which can independently vary in assignment at angle 2-theta in degrees as described herein. For example, Form IV may have an XRPD pattern comprising peaks each assigned at an angle 2-theta in degrees of about 4.14 (e.g., 4.14±0.2), about 20.02 (e.g., 20.02±0.2), about 21.57 (e.g., 21.57±0.2), about 6.64 (e.g., 6.64±0.2), about 25.22 (e.g., 25.22±0.2), about 15.18 (e.g., 15.18±0.2), about 21.79 (e.g., 21.79±0.2), about 11.20 (e.g., 11.20±0.2), about 11.65 (e.g., 11.65±0.2), about 24.86 (e.g., 24.86±0.2), about 17.18 (e.g., 17.18±0.2), about 19.17 (e.g., 19.17±0.2), about 23.42 (e.g., 23.42±0.2), about 20.39 (e.g., 20.39±0.2), about 16.69 (e.g., 16.69±0.2), about 25.03 (e.g., 25.03±0.2), about 9.78 (e.g., 9.78±0.2), about 22.89 (e.g., 22.89±0.2), about 23.62 (e.g., 23.62±0.2), about 12.53 (e.g., 12.53±0.2), about 23.96 (e.g., 23.96±0.2), about 20.76 (e.g., 20.76±0.2), about 14.60 (e.g., 14.60±0.2), about 22.16 (e.g., 22.16±0.2), about 21.31 (e.g., 21.31±0.2), about 28.25 (e.g., 28.25±0.2), about 17.71 (e.g., 17.71±0.2), about 12.43 (e.g., 12.43±0.2), about 26.72 (e.g., 26.72±0.2), and about 33.66 (e.g., 33.66±0.2). In some embodiments, Form IV has an XRPD pattern comprising one or more (e.g., at least one, at least two, at least three, at least four, at least five, at least six, at least seven, at least eight, at least nine, or at least ten) peaks each assigned at angles 2-theta in degrees of about: about 4.14 (e.g., 4.14±0.2), about 20.02 (e.g., 20.02±0.2), about 21.57 (e.g., 21.57±0.2), about 6.64 (e.g., 6.64±0.2), about 25.22 (e.g., 25.22±0.2), about 15.18 (e.g., 15.18±0.2), about 21.79 (e.g., 21.79±0.2), about 11.20 (e.g., 11.20±0.2), about 11.65 (e.g., 11.65±0.2), about 24.86 (e.g., 24.86±0.2), about 17.18 (e.g., 17.18±0.2), about 19.17 (e.g., 19.17±0.2), about 23.42 (e.g., 23.42±0.2), about 20.39 (e.g., 20.39±0.2), about 16.69 (e.g., 16.69±0.2), about 25.03 (e.g., 25.03±0.2), about 9.78 (e.g., 9.78±0.2), about 22.89 (e.g., 22.89±0.2), about 23.62 (e.g., 23.62±0.2), about 12.53 (e.g., 12.53±0.2), about 23.96 (e.g., 23.96±0.2), about 20.76 (e.g., 20.76±0.2), about 14.60 (e.g., 14.60±0.2), about 22.16 (e.g., 22.16±0.2), about 21.31 (e.g., 21.31±0.2), about 28.25 (e.g., 28.25±0.2), about 17.71 (e.g., 17.71±0.2), about 12.43 (e.g., 12.43±0.2), about 26.72 (e.g., 26.72±0.2), and about 33.66 (e.g., 33.66±0.2). In some embodiments, Form IV has an XRPD pattern comprising peaks each assigned at angles 2-theta in degrees of about 4.14 (e.g., 4.14±0.2), about 20.02 (e.g., 20.02±0.2), about 21.57 (e.g., 21.57±0.2), about 6.64 (e.g., 6.64±0.2), about 25.22 (e.g., 25.22±0.2), about 15.18 (e.g., 15.18±0.2), about 21.79 (e.g., 21.79±0.2), about 11.20 (e.g., 11.20±0.2), about 11.65 (e.g., 11.65±0.2), and about 24.86 (e.g., 24.86±0.2). In some embodiments, Form IV has an XRPD pattern comprising one or more (e.g., at least one, at least two, at least three, at least four, at least five, at least six, at least seven, at least eight, at least nine, or at least ten) peaks each assigned at angles 2-theta in degrees of about 4.14 (e.g., 4.14±0.2), about 20.02 (e.g., 20.02±0.2), about 21.57 (e.g., 21.57±0.2), about 6.64 (e.g., 6.64±0.2), about 25.22 (e.g., 25.22±0.2), about 15.18 (e.g., 15.18±0.2), about 21.79 (e.g., 21.79±0.2), about 11.20 (e.g., 11.20±0.2), about 11.65 (e.g., 11.65±0.2), and about 24.86 (e.g., 24.86±0.2). In some embodiments, Form IV has an XRPD pattern comprising peaks each assigned at angles 2-theta in degrees of about: 4.14 (e.g., 4.14±0.2), about 20.02 (e.g., 20.02±0.2), about 21.57 (e.g., 21.57±0.2), about 6.64 (e.g., 6.64±0.2), and about 25.22 (e.g., 25.22±0.2). In some embodiments, Form IV has an XRPD pattern comprising one or more (e.g., at least one, at least two, at least three, at least four, or at least five) peaks each assigned at angles 2-theta in degrees of about 4.14 (e.g., 4.14±0.2), about 20.02 (e.g., 20.02±0.2), about 21.57 (e.g., 21.57±0.2), about 6.64 (e.g., 6.64±0.2), and about 25.22 (e.g., 25.22±0.2). In some embodiments, Form IV has an XRPD pattern comprising peaks assigned at angles 2-theta in degrees of about 4.14, about 6.64, about 11.20, and about 15.18. In some embodiments, Form IV has an XRPD pattern comprising peaks assigned at angles 2-theta in degrees of about 4.14±0.2, about 6.64±0.2, about 11.20±0.2, and about 15.18=0.2. In some embodiments, Form IV has an XRPD pattern comprising peaks assigned at angles 2-theta in degrees of about 4.14, about 6.64, and about 11.20. In some embodiments, Form IV has an XRPD pattern comprising peaks assigned at angles 2-theta in degrees of about 4.14±0.2, about 6.64±0.2, and about 11.20±0.2. In some embodiments, Form IV has an XRPD pattern comprising peaks assigned at angles 2-theta in degrees of about 4.14, about 6.64, and about 15.18. In some embodiments, Form IV has an XRPD pattern comprising peaks assigned at angles 2-theta in degrees of about 4.14±0.2, about 6.64±0.2, and about 15.18±0.2. In some embodiments, Form IV has an XRPD pattern comprising peaks assigned at angles 2-theta in degrees of about 4.14 and about 6.64. In some embodiments, Form IV has an XRPD pattern comprising peaks assigned at angles 2-theta in degrees of about 4.14±0.2 and about 6.64±0.2. In some embodiments, Form IV has an XRPD pattern comprising a peak assigned at angle 2-theta in degrees of about 4.14. In some embodiments, Form IV has an XRPD pattern comprising a peak assigned at angle 2-theta in degrees of about 4.14±0.2.

In some embodiments of a crystalline form disclosed herein (e.g., Form I, II, III, or IV), the crystalline form is substantially anhydrous. For example, in some embodiments, the crystalline form has a water content of less than about 1%, about 0.5%, or about 0.1% by weight. In some embodiments, the crystalline form has a water content in % by weight of one of about 1, 1.5, 2, 2.5, 3, 3.5, 4, 4.5 5, 5.5, 6, 6.5, 7, 7.5 8, 8.5, 9, 9.5, or 10, or a range between any two of the preceding values. For example, the crystalline form can have a water content of about 1-10 wt %. The water content can be about 2-10 wt %. The water content can be about 3-10 wt %. The water content can be about 4-10 wt %. The water content can be about 5-10 wt %. The water content can be about 6-10 wt %. The water content can be about 7-10 wt %. The water content can be about 8-10 wt %. The water content can be about 9-10 wt %. The water content can be about 1-9 wt %. The water content can be about 2-9 wt %. The water content can be about 3-9 wt %. The water content can be about 4-9 wt %. The water content can be about 5-9 wt %. The water content can be about 6-9 wt %. The water content can be about 7-9 wt %. The water content can be about 8-9 wt %. The water content can be about 1-8 wt %. The water content can be about 2-8 wt %. The water content can be about 3-8 wt %. The water content can be about 4-8 wt %. The water content can be about 5-8 wt %. The water content can be about 6-8 wt %. The water content can be about 7-8 wt %. The water content can be about 1-7 wt %. The water content can be about 2-7 wt %. The water content can be about 3-7 wt %. The water content can be about 4-7 wt %. The water content can be about 5-7 wt %. The water content can be about 6-7 wt %. The water content can be about 1-6 wt %. The water content can be about 2-6 wt %. The water content can be about 3-6 wt %. The water content can be about 4-6 wt %. The water content can be about 5-6 wt %. The water content can be about 1-5 wt %. The water content can be about 2-5 wt %. The water content can be about 3-5 wt %. The water content can be about 4-5 wt %. The water content can be about 1-4 wt %. The water content can be about 2-4 wt %. The water content can be about 3-4 wt %. The crystalline form can have a water content that varies in % by weight of ±1, ±0.75, ±0.5, ±0.25, or ±0.1 around a % by weight of one of 1, 1.5, 2, 2.5, 3, 3.5, 4, 4.5 5, 5.5, 6, 6.5, 7, 7.5 8, 8.5, 9, 9.5, or 10. For example, the crystalline form can have a water content of about 1±0.75 wt %. The water content can be about 1±0.5 wt %. The water content can be about 1±0.25 wt %. The water content can be about 1±0.1 wt %. The water content can be about 1.5±1 wt %. The water content can be about 1.5±0.75 wt %. The water content can be about 1.5±0.5 wt %. The water content can be about 1.5±0.25 wt %. The water content can be about 1.5±0.1 wt %. The water content can be about 2±1 wt %. The water content can be about 2±0.75 wt %. The water content can be about 2±0.5 wt %. The water content can be about 2±0.25 wt %. The water content can be about 2±0.1 wt %. The water content can be about 2.5±1 wt %. The water content can be about 2.5±0.75 wt %. The water content can be about 2.5±0.5 wt %. The water content can be about 2.5±0.25 wt %. The water content can be about 2.5±0.1 wt %. The water content can be about 3±1 wt %. The water content can be about 3±0.75 wt %. The water content can be about 3±0.5 wt %. The water content can be about 3±0.25 wt %. The water content can be about 3±0.1 wt %. The water content can be about 3.5±1 wt %. The water content can be about 3.5±0.75 wt %. The water content can be about 3.5±0.5 wt %. The water content can be about 3.5±0.25 wt %. The water content can be about 3.5±0.1 wt %. The water content can be about 4±1 wt %. The water content can be about 4±0.75 wt %. The water content can be about 4±0.5 wt %. The water content can be about 4±0.25 wt %. The water content can be about 4±0.1 wt %. The water content can be about 4.5±1 wt %. The water content can be about 4.5±0.75 wt %. The water content can be about 4.5±0.5 wt %. The water content can be about 4.5±0.25 wt %. The water content can be about 4.5±0.1 wt %. The water content can be about 5±1 wt %. The water content can be about 5±0.75 wt %. The water content can be about 5±0.5 wt %. The water content can be about 5±0.25 wt %. The water content can be about 5±0.1 wt %. The water content can be about 5.5±1 wt %. The water content can be about 5.5±0.75 wt %. The water content can be about 5.5±0.5 wt %. The water content can be about 5.5±0.25 wt %. The water content can be about 5.5±0.1 wt %. The water content can be about 6±1 wt %. The water content can be about 6±0.5 wt %. The water content can be about 6.5±1 wt %. The water content can be about 6.5±0.5 wt %. The water content can be about 7±1 wt %. The water content can be about 7±0.5 wt %. The water content can be about 7.5±1 wt %. The water content can be about 7.5±0.5 wt %. The water content can be about 8±1 wt %. The water content can be about 8±0.5 wt %. The water content can be about 8.5±1 wt %. The water content can be about 8.5±0.5 wt %. The water content can be about 9±1 wt %. The water content can be about 9±0.5 wt %. The water content can be about 9.5±0.5 wt %. The water content can be about 9.5±0.25 wt %.

Methods of Preparation

Form I

In some embodiments, provided is a method of preparing Form I, comprising preparing a mixture of (S)-4-((2-methoxyethyl)(4-(5,6,7,8-tetrahydro-1,8-naphthyridin-2-yl)butyl)amino)-2-(quinazolin-4-ylamino)butanoic acid and phosphoric acid in a solvent. In some embodiments, the mixture is prepared as a slurry. In some embodiments, the solvent comprises an alcohol. In some embodiments, the solvent comprises ethanol. In some embodiments, the molar ratio of (S)-4-((2-methoxyethyl)(4-(5,6,7,8-tetrahydro-1,8-naphthyridin-2-yl)butyl)amino)-2-(quinazolin-4-ylamino) butanoic acid to phosphoric acid is about 1:1. In some embodiments, the method is conducted at room temperature. In some embodiments, the method of preparing Form I further comprises subjecting the mixture to one or more (e.g., one, two, three, four, or five) temperature cycles (e.g., 50° C. to 5° C. at 0.05° C./min, then 5° C. to 50° C. at 0.375° C./min for each cycle). In some embodiments, each temperature cycle comprises decreasing the temperature from about 50° C. to about 5° C. and increasing the temperature from about 5° C. to about 50° C. at about 0.375° C./min.

In some embodiments, provided is a method of preparing Form I, comprising converting (S)-4-((2-methoxyethyl)(4-(5,6,7,8-tetrahydro-1,8-naphthyridin-2-yl)butyl)amino)-2-(quinazolin-4-ylamino)butanoic acid zwitterion (ZI) to Form I. In some embodiments, converting (S)-4-((2-methoxyethyl)(4-(5,6,7,8-tetrahydro-1,8-naphthyridin-2-yl)butyl)amino)-2-(quinazolin-4-ylamino)butanoic acid ZI to Form I comprises mixing (S)-4-((2-methoxyethyl)(4-(5,6,7,8-tetrahydro-1,8-naphthyridin-2-yl)butyl)amino)-2-(quinazolin-4-ylamino)butanoic acid ZI and phosphoric acid in a solvent. In some embodiments, the solvent comprises an alcohol. In some embodiments, the solvent comprises 1:4 methanol/ethanol (v/v). In some embodiments, mixing (S)-4-((2-methoxyethyl)(4-(5,6,7,8-tetrahydro-1,8-naphthyridin-2-yl)butyl)amino)-2-(quinazolin-4-ylamino)butanoic acid ZI and phosphoric acid comprises: (a1) mixing (S)-4-((2-methoxyethyl)(4-(5,6,7,8-tetrahydro-1,8-naphthyridin-2-yl)butyl)amino)-2-(quinazolin-4-ylamino)butanoic acid ZI with phosphoric acid (about 0.25 eq.), (b1) adding a seed of Form I, and (c1) adding phosphoric acid (about 0.8 eq.) to the mixture of step (b1). In some embodiments, the mixture of step (c1) is stored at about 30° C. for about 2 hours and then stored at 20° C. for about 2 hours. In some embodiments, the method of preparing Form I further comprising converting a hydrochloride salt of benzyl (S)-4-((2-methoxyethyl)(4-(5,6,7,8-tetrahydro-1,8-naphthyridin-2-yl)butyl)amino)-2-(quinazolin-4-ylamino)butanoate to the (S)-4-((2-methoxyethyl)(4-(5,6,7,8-tetrahydro-1,8-naphthyridin-2-yl)butyl)amino)-2-(quinazolin-4-ylamino) butanoic acid ZI. In some embodiments, the hydrochloride salt is a dihydrochloride salt. In some embodiments, converting the hydrochloride salt of benzyl (S)-4-((2-methoxyethyl)(4-(5,6,7,8-tetrahydro-1,8-naphthyridin-2-yl)butyl)amino)-2-(quinazolin-4-ylamino)butanoate to the (S)-4-((2-methoxyethyl)(4-(5,6,7,8-tetrahydro-1,8-naphthyridin-2-yl)butyl)amino)-2-(quinazolin-4-ylamino)butanoic acid ZI comprises: (a2) dissolving the hydrochloride salt of benzyl (S)-4-((2-methoxyethyl)(4-(5,6,7,8-tetrahydro-1,8-naphthyridin-2-yl)butyl)amino)-2-(quinazolin-4-ylamino)butanoate in a concentrated hydrochloric acid solution, and (b2) adjusting the pH of the mixture of step (a2) to 7.2-7.6. In some embodiments, the step of adjusting the pH of the mixture of step (a2) comprises adding NaOH and/or $NaHCO_3$ to the mixture of step (a2). In some embodiments, converting the hydrochloride salt of benzyl (S)-4-((2-methoxyethyl)(4-(5,6,7,8-tetrahydro-1,8-naphthyridin-2-yl)butyl)amino)-2-(quinazolin-4-ylamino)butanoate to the (S)-4-((2-methoxyethyl)(4-(5,6,7,8-tetrahydro-1,8-naphthyridin-2-yl)butyl)amino)-2-(quinazolin-4-ylamino) butanoic acid ZI further comprises extracting the ZI with an organic solvent. In some embodiments, the organic solvent is DCM.

Form II

In some embodiments, provided is a method of preparing Form II, comprising preparing a mixture of (S)-4-((2-methoxyethyl)(4-(5,6,7,8-tetrahydro-1,8-naphthyridin-2-yl)butyl)amino)-2-(quinazolin-4-ylamino)butanoic acid and fumaric acid in a solvent. In some embodiments, the mixture is prepared as a slurry. In some embodiments, the solvent comprises a ketone (e.g., acetone), water, or a mixture thereof. In some embodiments, the solvent comprises a mixture of acetone and water. In some embodiments, the acetone to water is about 19:1 (v/v). In some embodiments, the method of preparing Form II further comprises subjecting the mixture to one or more (e.g., one, two, three, four, or five) temperature cycles (e.g., 50° C. to 5° C. at 0.05° C./min, then 5° C. to 50° C. at 0.375° C./min for each cycle). In some embodiments, each temperature cycle comprises decreasing the temperature from about 50° C. to about 5° C. and increasing the temperature from about 5° C. to about 50° C. at about 0.375° C./min.

Form III

In some embodiments, provided is a method of preparing Form III, comprising preparing a mixture of (S)-4-((2-methoxyethyl)(4-(5,6,7,8-tetrahydro-1,8-naphthyridin-2-yl)butyl)amino)-2-(quinazolin-4-ylamino)butanoic acid and 1,5-naphthalenedisulfonic acid in a solvent. In some embodiments, the mixture is prepared as a slurry. In some embodiments, the solvent comprises an acetate (e.g., isopropyl acetate or ethyl acetate). In some embodiments, the solvent comprises ethyl acetate. In some embodiments, the method is conducted at room temperature.

Form IV

In some embodiments, provided is a method of preparing Form IV, comprising preparing a mixture of (S)-4-((2-methoxyethyl)(4-(5,6,7,8-tetrahydro-1,8-naphthyridin-2-yl)butyl)amino)-2-(quinazolin-4-ylamino)butanoic acid and phosphoric acid (e.g., in a 1:1 mole ratio) in a solvent comprising isopropyl alcohol. In some embodiments, the solvent comprises water effective to incorporate the water into Form IV. In some embodiments, the solvent comprises methanol. In some embodiments, the method is conducted under an atmosphere comprising water effective to allow water from the atmosphere to be incorporated into Form IV. In some embodiments, the method is conducted at room temperature.

In some embodiments of a method of preparing a crystalline form disclosed herein (e.g., Form I, II, III, or IV), the method further comprises preparing (e.g., drying) the crystalline form such that the crystalline form is substantially anhydrous. For example, in some embodiments, the method further comprises preparing the crystalline form such that the crystalline form has a water content of less than about 1%, about 0.5%, or about 0.1% by weight. In some embodiments, the method further comprises preparing the crystalline form such that the crystalline form has a water content in % by weight of one of about 1, 1.5, 2, 2.5, 3, 3.5, 4, 4.5 5, 5.5, 6, 6.5, 7, 7.5 8, 8.5, 9, 9.5, or 10, or a range between any two of the preceding values. In some embodiments, the method comprises a humidification step. For example, the crystalline form can have a water content of about 1-10 wt %. The water content can be about 2-10 wt %. The water content can be about 3-10 wt %. The water content can be about 4-10 wt %. The water content can be about 5-10 wt %. The water content can be about 6-10 wt %. The water content can be about 7-10 wt %. The water content can be about 8-10 wt %. The water content can be about 9-10 wt %. The water content can be about 1-9 wt %. The water content can be about 2-9 wt %. The water content can be about 3-9 wt %. The water content can be about 4-9 wt %. The water content can be about 5-9 wt %. The water content can be about 6-9 wt %. The water content can be about 7-9 wt %. The water content can be about 8-9 wt %. The water content can be about 1-8 wt %. The water content can be about 2-8 wt %. The water content can be about 3-8 wt %. The water content can be about 4-8 wt %. The water content can be about 5-8 wt %. The water content can be about 6-8 wt %. The water content can be about 7-8 wt %. The water content can be about 1-7 wt %. The water content can be about 2-7 wt %. The water content can be about 3-7 wt %. The water content can be about 4-7 wt %. The water content can be about 5-7 wt %. The water content can be about 6-7 wt %. The water content can be about 1-6 wt %. The water content can be about 2-6 wt %. The water content can be about 3-6 wt %. The water content can be about 4-6 wt %. The water content can be about 5-6 wt %. The water content can be about 1-5 wt %. The water content can be about 2-5 wt %. The water content can be about 3-5 wt %. The water content can be about 4-5 wt %. The water content can be about 1-4 wt %. The water content can be about 2-4 wt %. The water content can be about 3-4 wt %. The crystalline form can have a water content that varies in % by weight of ±1, ±0.75, ±0.5, ±0.25, or ±0.1 around a % by weight of one of 1, 1.5, 2, 2.5, 3, 3.5, 4, 4.5 5, 5.5, 6, 6.5, 7, 7.5 8, 8.5, 9, 9.5, or 10. For example, the crystalline form can have a water content of about 1±0.75 wt %. The water content can be about 1±0.5 wt %. The water content can be about 1±0.25 wt %. The water content can be about 1±0.1 wt %. The water content can be about 1.5±1 wt %. The water content can be about 1.5±0.75 wt %. The water content can be about 1.5±0.5 wt %. The water content can be about 1.5±0.25 wt %. The water content can be about 1.5±0.1 wt %. The water content can be about 2±1 wt %. The water content can be about 2±0.75 wt %. The water content can be about 2±0.5 wt %. The water content can be about 2±0.25 wt %. The water content can be about 2±0.1 wt %. The water content can be about 2.5±1 wt %. The water content can be about 2.5±0.75 wt %. The water content can be about 2.5±0.5 wt %. The water content can be about 2.5±0.25 wt %. The water content can be about 2.5±0.1 wt %. The water content can be about 3±1 wt %. The water content can be about 3±0.75 wt %. The water content can be about 3±0.5 wt %. The water content can be about 3±0.25 wt %. The water content can be about 3±0.1 wt %. The water content can be about 3.5±1 wt %. The water content can be about 3.5±0.75 wt %. The water content can be about 3.5±0.5 wt %. The water content can be about 3.5±0.25 wt %. The water content can be about 3.5±0.1 wt %. The water content can be about 4±1 wt %. The water content can be about 4±0.75 wt %. The water content can be about 4±0.5 wt %. The water content can be about 4±0.25 wt %. The water content can be about 4±0.1 wt %. The water content can be about 4.5±1 wt %. The water content can be about 4.5±0.75 wt %. The water content can be about 4.5±0.5 wt %. The water content can be about 4.5±0.25 wt %. The water content can be about 4.5±0.1 wt %. The water content can be about 5±1 wt %. The water content can be about 5±0.75 wt %. The water content can be about 5±0.5 wt %. The water content can be about 5±0.25 wt %. The water content can be about 5±0.1 wt %. The water content can be about 5.5±1 wt %. The water content can be about 5.5±0.75 wt %. The water content can be about 5.5±0.5 wt %. The water content can be about 5.5±0.25 wt %. The water content can be about 5.5±0.1 wt %. The water content can be about 6±1 wt %. The water content can be about 6±0.5 wt %. The water content can be about 6.5±1 wt %. The water content can be about 6.5±0.5 wt %. The water content can be about 7±1 wt %. The water content can be about 7±0.5 wt %. The water content can be about 7.5±1 wt %. The water content can be about 7.5±0.5 wt %. The water content can be about 8±1 wt %. The water content can be about 8±0.5 wt %. The water content can be about 8.5±1 wt %. The water content can be about 8.5±0.5 wt %. The water content can be about 9±1 wt %. The water content can be about 9±0.5 wt %. The water content can be about 9.5±0.5 wt %. The water content can be about 9.5±0.25 wt %.

Pharmaceutical Compositions and Formulations

Pharmaceutical compositions of any of crystalline forms detailed herein, including Form I, Form II, Form III, or Form IV, are embraced by this invention. Thus, the invention includes pharmaceutical compositions comprising a crystalline form disclosed herein (e.g., Form I, Form II, Form III, or Form IV) and a pharmaceutically acceptable carrier or excipient. In one embodiment, the pharmaceutical composition is a composition for controlled release of any of the crystalline forms detailed herein.

In some embodiments, provided is a composition comprising Form I. In some embodiments, the composition is substantially free of amorphous or non-crystalline form of (S)-4-((2-methoxyethyl)(4-(5,6,7,8-tetrahydro-1,8-naphthyridin-2-yl)butyl)amino)-2-(quinazolin-4-ylamino)butanoic acid or a salt thereof. In some embodiments of the composition comprising Form I, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least 99.9% by weight of the total composition is Form I. In some embodiments of the composition comprising Form I, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least 99.9% by weight of (S)-4-((2-methoxyethyl)(4-(5,6,7,8-tetrahydro-1,8-naphthyridin-2-yl)butyl)amino)-2-(quinazolin-4-ylamino)butanoic acid exists in Form I.

In some embodiments, provided is a composition comprising Form II. In some embodiments, the composition is substantially free of amorphous or non-crystalline form of (S)-4-((2-methoxyethyl)(4-(5,6,7,8-tetrahydro-1,8-naphthyridin-2-yl)butyl)amino)-2-(quinazolin-4-ylamino)butanoic acid or a salt thereof. In some embodiments of the composition comprising Form II, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least 99.9% by weight of the total composition is Form II. In some embodiments of the composition comprising Form II, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least 99.9% by weight of (S)-4-((2-methoxyethyl)(4-(5,6,7,8-tetrahydro-1,8-naphthyridin-2-yl)butyl)amino)-2-(quinazolin-4-ylamino)butanoic acid exists in Form II.

In some embodiments, provided is a composition comprising Form III. In some embodiments, the composition is substantially free of amorphous or non-crystalline form of (S)-4-((2-methoxyethyl)(4-(5,6,7,8-tetrahydro-1,8-naphthyridin-2-yl)butyl)amino)-2-(quinazolin-4-ylamino)butanoic acid or a salt thereof. In some embodiments of the composition comprising Form III, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least 99.9% by weight of the total composition is Form III. In some embodiments of the composition comprising Form III, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least 99.9% by weight of (S)-4-((2-methoxyethyl)(4-(5,6,7,8-tetrahydro-1,8-naphthyridin-2-yl)butyl)amino)-2-(quinazolin-4-ylamino)butanoic acid exists in Form III.

In some embodiments, provided is a composition comprising Form IV. In some embodiments, the composition is substantially free of amorphous or non-crystalline form of (S)-4-((2-methoxyethyl)(4-(5,6,7,8-tetrahydro-1,8-naphthyridin-2-yl)butyl)amino)-2-(quinazolin-4-ylamino)butanoic acid or a salt thereof. In some embodiments of the composition comprising Form IV, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least 99.9% by weight of the total composition is Form IV. In some embodiments of the composition comprising Form IV, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least 99.9% by weight of (S)-4-((2-methoxyethyl)(4-(5,6,7,8-tetrahydro-1,8-naphthyridin-2-yl)butyl)amino)-2-(quinazolin-4-ylamino)butanoic acid exists in Form IV.

Crystalline forms or compositions disclosed herein may be formulated for any available delivery route, including an oral, mucosal (e.g., nasal, sublingual, vaginal, buccal or rectal), parenteral (e.g., intramuscular, subcutaneous or intravenous), topical or transdermal delivery form, or a form suitable for inhalation. A crystalline form or composition disclosed herein may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

Crystalline forms disclosed herein can be used in the preparation of a formulation, such as a pharmaceutical formulation, by combining the crystalline form as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington: The Science and Practice of Pharmacy*, Lippincott Williams & Wilkins, 21$^{st}$ ed. (2005), which is incorporated herein by reference.

Crystalline forms disclosed herein may be administered to individuals (e.g., a human) in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Crystalline forms disclosed herein can be formulated in a tablet in any dosage form described, for example, a crystalline form can be formulated as a 10 mg tablet. Exemplary dosages for crystalline forms disclosed herein are disclosed in U.S. patent application Ser. No. 16/843,824, published as US Pat. App. Pub. No. 2020-0352942, hereby incorporated herein by reference in its entirety.

In various embodiments, a dose, e.g., a unit dose, such as a unit dose for daily administration, can include the crystalline form in an amount of one of, or one of about: 1, 2.5, 5, 7.5, 10, 15, 20, 25, 30, 35, 40, 45, 50, 55, 60, 75, 80, 85, 90, 95, 100, 105, 110, 115, 120, 125, 130, 140, 150, 160, 170, 175, 180, 190, 200, 225, 240, 250, 275, 300, 320, 325, 350, 375, 400, 425, 450, 475, 480, 500, 525, 550, 560, 575, 600, 625, 640, 650, 675, 700, 720, 725, 750, 775 800, 825, 850, 875, 880, 900, 925, 950, 960, 975, 1000, 1025, or 1040 milligrams. For example, a dose can include the crystalline form in an amount of, or of about, 10 mg. A dose can include the crystalline form in an amount of, or of about, 15 mg. A dose can include the crystalline form in an amount of, or of about, 20 mg. A dose can include the crystalline form in an amount of, or of about, 30 mg. A dose can include the crystalline form in an amount of, or of about, 40 mg. A dose can include the crystalline form in an amount of, or of about, 50 mg. A dose can include the crystalline form in an amount of, or of about, 75 mg. A dose can include the crystalline form in an amount of, or of about, 80 mg. A dose can include the crystalline form in an amount of, or of about, 100 mg. A dose can include the crystalline form in an amount of, or of about, 120 mg. A dose can include the crystalline form in an amount of, or of about, 160 mg. A dose can include the crystalline form in an amount of, or of about, 240 mg. A dose can include the crystalline form in an amount of, or of about, 320 mg. A dose can include the crystalline form in an amount of, or of about, 400 mg. A dose can include the crystalline form in an amount of, or of about, 480 mg. A dose can include the crystalline form in an amount of, or of about, 560 mg. A dose can include the crystalline form in an amount of, or of about, 640 mg. A dose can include the crystalline form in an amount of, or of about, 720 mg. A dose can include the crystalline form in an amount of, or of about, 800 mg. A dose can include the crystalline form in an amount of, or of about, 880 mg. A dose can include the crystalline form in an amount of, or of about, 960 mg. A dose can include the crystalline form in an amount of, or of about, 1040 mg.

In various embodiments, a dose, e.g., a unit dose, such as a unit dose for daily administration, can include the crystalline form in an amount comprising an amount of the crystalline form in mg of about one of about: 320, 400, 480, 560, 640, 720, 800, 880, 960, or 1040, or a range between any two of the preceding values.

In various embodiments, a dose, e.g., a unit dose, such as a unit dose for daily administration, can include the crystalline form in an amount comprising an amount of the crystalline form in mg of about one of about: 400, 480, 560, 640, 720, 800, 880, 960, or 1040.

In various embodiments, a dose, e.g., a unit dose, such as a unit dose for daily administration, can include the crystalline form in an amount comprising an amount of the crystalline form in mg of a range between about 320 and any one of about 400, 480, 560, 640, 720, 800, 880, 960, or 1040.

In various embodiments, a dose, e.g., a unit dose, such as a unit dose for daily administration, can include the crystalline form in an amount comprising an amount of the crystalline form in mg of about one of: 400, 480, 560, 640, 720, 800, 880, 960, or 1040, or a range between any two of the preceding values.

In some embodiments, the unit dose may include the crystalline form in a percentage range about any of the individual values in milligrams recited in the preceding paragraph, for example, any percentage range independently selected from one of, or one of about:±1%, ±2%, ±2.5%, ±5%, ±7.5%, ±10%, ±15%, ±20%, ±25%, ±30%, ±40%, or ±50%. For example, the range may be, or be about, ±1%. The range may be, or be about, ±2%. The range may be, or be about, ±2.5%. The range may be, or be about, ±5%. The range may be, or be about, ±7.5%. The range may be, or be about, ±10%. The range may be, or be about, ±15%. The range may be, or be about, ±20%. The range may be, or be about, ±25%. The range may be, or be about, ±30%. The range may be, or be about, ±40%. The range may be, or be about, ±50%.

Further, for example, the unit dose may include the crystalline form in an amount of one of: 10 mg±1%; 10 mg±2%; 10 mg±2.5%; 10 mg±5%; 10 mg±7.5%; 10 mg±10%; 10 mg±15%; 10 mg±20%; 10 mg±25%; 10 mg±30%; 10 mg±40%; or 10 mg±50%. The unit dose may include the crystalline form in an amount of one of: 15 mg±1%; 15 mg±2%; 15 mg±2.5%; 15 mg±5%; 15 mg±7.5%; 15 mg±10%; 15 mg±15%; 15 mg±20%; 15 mg±25%; 15 mg±30%; 15 mg±40%; or 15 mg±50%. The unit dose may include the crystalline form in an amount of one of: 20 mg±1%; 20 mg±2%; 20 mg±2.5%; 20 mg±5%; 20 mg±7.5%; 20 mg±10%; 20 mg±15%; 20 mg±20%; 20 mg±25%; 20 mg±30%; 20 mg±40%; or 20 mg±50%. The unit dose may include the crystalline form in an amount of one of: 30 mg±1%; 30 mg±2%; 30 mg±2.5%; 30 mg±5%; 30 mg±7.5%; 30 mg±10%; 30 mg±15%; 30 mg±20%; 30 mg±25%; 30 mg±30%; 30 mg±40%; or 30 mg±50%. The unit dose may include the crystalline form in an amount of one of: 40 mg±1%; 40 mg±2%; 40 mg±2.5%; 40 mg±5%; 40 mg±7.5%; 40 mg±10%; 40 mg±15%; 40 mg±20%; 40 mg±25%; 40 mg±30%; 40 mg±40%; or 40 mg±50%. The unit dose may include the crystalline form in an amount of one of: 50 mg±1%; 50 mg±2%; 50 mg±2.5%; 50 mg±5%; 50 mg±7.5%; 50 mg±10%; 50 mg±15%; 50 mg±20%; 50 mg±25%; 50 mg±30%; 50 mg±40%; or 50 mg±50%. The unit dose may include the crystalline form in an amount of one of: 60 mg±1%; 60 mg±2%; 60 mg±2.5%; 60 mg±5%; 60 mg±7.5%; 60 mg±10%; 60 mg±15%; 60 mg±20%; 60 mg±25%; 60 mg±30%; 60 mg±40%; or 60 mg±50%. The unit dose may include the crystalline form in an amount of one of: 75 mg±1%; 75 mg±2%; 75 mg±2.5%; 75 mg±5%; 75 mg±7.5%; 75 mg±10%; 75 mg±15%; 75 mg±20%; 75 mg±25%; 75 mg±30%; 75 mg±40%; or 75 mg±50%. The unit dose may include the crystalline form in an amount of one of: 80 mg±1%; 80 mg±2%; 80 mg±2.5%; 80 mg±5%; 80 mg±7.5%; 80 mg±10%; 80 mg±15%; 80 mg±20%; 80 mg±25%; 80 mg±30%; 80 mg±40%; or 80 mg±50%. The unit dose may include the crystalline form in an amount of one of: 100 mg±1%; 100 mg±2%; 100 mg±2.5%; 100 mg±5%; 100 mg±7.5%; 100 mg±10%; 100 mg±15%; 100 mg±20%; 100 mg±25%; 100 mg±30%; 100 mg±40%; or 100 mg±50%. The unit dose may include the crystalline form in an amount of one of: 120 mg±1%; 120 mg±2%; 120 mg±2.5%; 120 mg±5%; 120 mg±7.5%; 120 mg±10%; 120 mg±15%; 120 mg±20%; 120 mg±25%; 120 mg±30%; 120 mg±40%; or 120 mg±50%. The unit dose may include the crystalline form in an amount of one of: 160 mg±1%; 160 mg±2%; 160 mg±2.5%; 160 mg±5%; 160 mg±7.5%; 160 mg±10%; 160 mg±15%; 160 mg±20%; 160 mg±25%; 160 mg±30%; 160 mg±40%; or 160 mg±50%. The unit dose may include the crystalline form in an amount of one of: 240 mg±1%; 240 mg±2%; 240 mg±2.5%; 240 mg±5%; 240 mg±7.5%; 240 mg±10%; 240 mg±15%; 240 mg±20%; 240 mg±25%; 240 mg±30%; 240 mg±40%; or 240 mg±50%. The unit dose may include the crystalline form in an amount of one of: 320 mg±1%; 320 mg±2%; 320 mg±2.5%; 320 mg±5%; 320 mg±7.5%; 320 mg±10%; 320 mg±15%; 320 mg±20%; 320 mg±25%; 320 mg±30%; 320 mg±40%; or 320 mg±50%. The unit dose may include the crystalline form in an amount of one of: 400 mg±1%; 400 mg±2%; 400 mg±2.5%; 400 mg±5%; 400 mg±7.5%; 400 mg±10%; 400 mg±15%; 400 mg±20%; 400 mg±25%; 400 mg±30%; 400 mg±40%; or 400 mg±50%. The unit dose may include the crystalline form in an amount of one of: 480 mg±1%; 480 mg±2%; 480 mg±2.5%; 480 mg±5%; 480 mg±7.5%; 480 mg±10%; 480 mg±15%; 480 mg±20%; 480 mg±25%; 480 mg±30%; 480 mg±40%; or 480 mg±50%. The unit dose may include the crystalline form in an amount of one of: 560 mg±1%; 560 mg±2%; 560 mg±2.5%; 560 mg±5%; 560 mg±7.5%; 560 mg±10%; 560 mg±15%; 560 mg±20%; 560 mg±25%; 560 mg±30%; 560 mg±40%; or 560 mg±50%. The unit dose may include the crystalline form in an amount of one of: 640 mg±1%; 640 mg±2%; 640 mg±2.5%; 640 mg±5%; 640 mg±7.5%; 640 mg±10%; 640 mg±15%; 640 mg±20%; 640 mg±25%; 640 mg±30%; 640 mg±40%; or 640 mg±50%. The unit dose may include the crystalline form in an amount of one of: 720 mg±1%; 720 mg±2%; 720 mg±2.5%; 720 mg±5%; 720 mg±7.5%; 720 mg±10%; 720 mg±15%; 720 mg±20%; 720 mg±25%; 720 mg±30%; 720 mg±40%; or 720 mg±50%. The unit dose may include the crystalline form in an amount of one of: 800 mg±1%; 800 mg±2%; 800 mg±2.5%; 800 mg±5%; 800 mg±7.5%; 800 mg±10%; 800 mg±15%; 800 mg±20%; 800 mg±25%; 800 mg±30%; 800 mg±40%; or 800 mg±50%. The unit dose may include the crystalline form in an amount of one of: 880 mg±1%; 880 mg±2%; 880 mg±2.5%; 880 mg±5%; 880 mg±7.5%; 880 mg±10%; 880 mg±15%; 880 mg±20%; 880 mg±25%; 880 mg±30%; 880 mg±40%; or 880 mg±50%. The unit dose may include the crystalline form in an amount of one of: 960 mg±1%; 960 mg±2%; 960 mg±2.5%; 960 mg±5%; 960 mg±7.5%; 960 mg±10%; 960 mg±15%; 960 mg±20%; 960 mg±25%; 960 mg±30%; 960 mg±40%; or 960 mg±50%. The unit dose may include the crystalline form in an amount of one of: 1040 mg±1%; 1040 mg±2%; 1040 mg±2.5%; 1040 mg±5%; 1040 mg±7.5%; 1040 mg±10%; 1040 mg±15%; 1040 mg±20%; 1040 mg±25%; 1040 mg±30%; 1040 mg±40%; or 1040 mg±50%.

A unit dose, such as a unit dose for daily administration, can comprise the crystalline form in an amount effective on administration to an individual to produce a $C_{max}$ in plasma of the individual in ng/ml of at least about, or greater than about, one of: 700, 750, 800, 850, 900, 950, 1000, 1050, 1100, 1150, 1200, 1250, 1300, 1350, 1400, 1450, 1500, 1600, 1700, 1800, 1900, 2000, 2100, 2200, 2300, 2400, or 2500; or a range between any two of the preceding concentrations, such as 700-1500, 700-900, 800-1300, 750-950, 800-1000, 850-950, 850-1050, 900-1400, 900-1300, 900-1200, 900-1100, 950-1050, 950-1400, 950-1150, 1000-1400, 1000-1300, 1000-1200, 700-2500, 1000-2500, 1500-2500, 1500-2000, 1500-2500, 2000-2500, and the like. For example, $C_{max}$ can be, or be about, about 700 ng/ml or greater. $C_{max}$ can be, or be about, about 750 ng/ml or greater. $C_{max}$ can be, or be about, about 800 ng/ml or greater. $C_{max}$ can be, or be about, 850 ng/ml or greater. $C_{max}$ can be, or be about, 900 ng/ml or greater. $C_{max}$ can be, or be about, 950 ng/ml or greater. $C_{max}$ can be, or be about, 1000 ng/ml or greater. $C_{max}$ can be, or be about, 1050 ng/ml or greater. $C_{max}$ can be, or be about, 1100 ng/ml or greater. $C_{max}$ can be, or be about, 1200 ng/mL or greater. $C_{max}$ can be, or be about, 1300 ng/ml or greater. $C_{max}$ can be, or be about, 1400 ng/ml or greater. $C_{max}$ can be, or be about, 1500 ng/mL or greater. $C_{max}$ can be, or be about, 1600 ng/ml or greater. $C_{max}$ can be, or be about, 1700 ng/ml or greater. $C_{max}$ can be, or be about, 1800 ng/ml or greater. $C_{max}$ can be, or be about, 1900 ng/ml or greater. $C_{max}$ can be, or be about, 2000 ng/ml or greater. $C_{max}$ can be, or be about, 2100 ng/ml or greater. $C_{max}$ can be, or be about, 2200 ng/ml or greater. $C_{max}$ can be, or be about, 2300 ng/ml or greater. $C_{max}$ can be, or be about, 2400 ng/ml or greater. $C_{max}$ can be, or be about, 2500 ng/ml or greater.

A unit dose, such as a unit dose for daily administration, can comprise the crystalline form in an amount effective on administration to an individual to produce a $C_{max}$ in plasma of the individual in ng/ml of at least about one of 700, 750, 800, 850, 900, 950, 1000, 1050, 1100, 1150, 1200, 1250, 1300, 1350, 1400, 1450, or 1500, or a range between any two of the preceding concentrations A unit dose, such as a unit dose for daily administration, can comprise the crystalline form in an amount effective on administration to an individual to produce a $C_{max}$ in plasma of the individual in ng/mL in a range between of at least about any one of 700, 750, 800, 850, 900, 950, 1000, 1050, 1100, 1150, 1200, 1250, 1300, 1350, 1400, or 1450 as a lower limit and 1500 as an upper limit.

A unit dose, such as a unit dose for daily administration, can comprise the crystalline form in an amount effective on administration to an individual to produce a $C_{max}$ in plasma of the individual in ng/ml of at least about one of: 1500, 1600, 1700, 1800, 1900, 2000, 2100, 2200, 2300, 2400, or 2500, or a range between any two of the preceding concentrations.

A unit dose, such as a unit dose for daily administration, can comprise the crystalline form in an amount effective on administration to an individual to produce a $C_{max}$ in plasma of the individual in ng/ml of at least about one of: 1600, 1700, 1800, 1900, 2000, 2100, 2200, 2300, 2400, or 2500, or a range between any two of the preceding concentrations;

A unit dose, such as a unit dose for daily administration, can comprise the crystalline form in an amount effective on administration to an individual to produce a $C_{max}$ in plasma of the individual in ng/ml in a range between at least 1500 and any one of 1600, 1700, 1800, 1900, 2000, 2100, 2200, 2300, 2400, or 2500.

A unit dose, such as a unit dose for daily administration, can comprise the crystalline form in an amount effective on administration to an individual to produce a $C_{max}$ in ng/ml in plasma of the individual, the $C_{max}$ corresponding to a plasma-adjusted concentration effective to inhibit a percentage of $\alpha_v\beta_6$ or $\alpha_v\beta_1$ in the individual of at least one of, or at least about one of: 50, 55, 60, 65, 70, 75, 80, 85, 90, 95, 97, 98, 99, or 100, or a range between any two of the preceding percentages, for example, 50-100, 60-90, 70-90, 75-95, 90-95, 90-98, 90-99, and the like. In some embodiments, the crystalline form may be a dual $\alpha_v\beta_6$ and $\alpha_v\beta_1$ inhibitor, and the $C_{max}$ can correspond to a plasma-adjusted concentration effective to inhibit a percentage of each of $\alpha_v\beta_6$ and $\alpha_v\beta_1$ in the individual, each percentage independently selected from the preceding percentages, or a range between any two of the preceding percentages. For example, the plasma-adjusted concentration can be effective to inhibit $\alpha_v\beta_6$ by at least about 50%. The plasma-adjusted concentration can be effective to inhibit $\alpha_v\beta_6$ by at least about 60%. The plasma-adjusted concentration can be effective to inhibit $\alpha_v\beta_6$ by at least about 70%. The plasma-adjusted concentration can be effective to inhibit $\alpha_v\beta_6$ by at least about 80%. The plasma-adjusted concentration can be effective to inhibit $\alpha_v\beta_6$ by at least about 90%. The plasma-adjusted concentration can be effective to inhibit $\alpha_v\beta_6$ by at least about 95%. The plasma-adjusted concentration can be effective to inhibit $\alpha_v\beta_6$ by at least about 97%. The plasma-adjusted concentration can be effective to inhibit $\alpha_v\beta_6$ by at least about 98%. The plasma-adjusted concentration can be effective to inhibit $\alpha_v\beta_6$ by at least about 99%. The plasma-adjusted concentration can be effective to inhibit $\alpha_v\beta_6$ by about 100%. Further, for example, the plasma-adjusted concentration can be effective to inhibit $\alpha_v\beta_1$ by at least about 50%. The plasma-adjusted concentration can be effective to inhibit $\alpha_v\beta_1$ by at least about 60%. The plasma-adjusted concentration can be effective to inhibit $\alpha_v\beta_1$ by at least about 70%. The plasma-adjusted concentration can be effective to inhibit $\alpha_v\beta_1$ by at least about 80%. The plasma-adjusted concentration can be effective to inhibit $\alpha_v\beta_1$ by at least about 90%. The plasma-adjusted concentration can be effective to inhibit $\alpha_v\beta_1$ by at least about 95%. The plasma-adjusted concentration can be effective to inhibit $\alpha_v\beta_1$ by at least about 97%. The plasma-adjusted concentration can be effective to inhibit $\alpha_v\beta_1$ by at least about 98%. The plasma-adjusted concentration can be effective to inhibit $\alpha_v\beta_1$ by at least about 99%. The plasma-adjusted concentration can be effective to inhibit $\alpha_v\beta_1$ by about 100%. The recitation "percentage of each of $\alpha_v\beta_6$ and/or $\alpha_v\beta_1$ in the subject, each percentage independently selected" means, in the alternative, a single $\alpha_v\beta_6$ inhibitor and corresponding percentage, a single $\alpha_v\beta_1$ inhibitor and corresponding percentage, or a dual $\alpha_v\beta_6/\alpha_v\beta_6$ inhibitor and corresponding independently selected percentages.

The dosage form for daily administration can be administered to an individual in need thereof once daily. That is, the total amount of a crystalline form that is to be administered each day can be administered all together at one time daily. Alternatively, if it is desirable that the total amount of a crystalline form is to be administered in two or more portions daily, the dosage form containing the appropriate amount of crystalline form can be administered two times or more daily, such as twice a day, three times a day, or four times a day.

Compositions comprising a crystalline form disclosed herein are also described. In some embodiments, the composition is for use as a human or veterinary medicament. In some embodiments, the composition is for use in a method described herein. In some embodiments, the composition is for use in the treatment of a disease or disorder described herein.

Methods of Use

Crystalline forms and compositions disclosed herein may be used in methods of administration and treatment as provided herein. The crystalline forms and compositions may also be used in *in vitro* methods, such as *in vitro* methods of administering a compound or composition to cells for screening purposes and/or for conducting quality control assays.

In some embodiments, provided is a method of treating a fibrotic disease in an individual in need thereof comprising administering to the individual a therapeutically effective amount of a crystalline form disclosed herein (e.g., Form I, Form II, Form III, or Form IV). In some embodiments, the individual is a human. The individual, such as human, may be in need of treatment, such as a human who has or is suspected of having a fibrotic disease.

In some embodiments, provided is a method of delaying the onset and/or development of a fibrotic disease in an individual (such as a human) who is at risk for developing a fibrotic disease, comprising administering to the individual a therapeutically effective amount of a crystalline form disclosed herein (e.g., Form I, Form II, Form III, or Form IV). It is appreciated that delayed development may encompass prevention in the event the individual does not develop the fibrotic disease. An individual at risk of developing a fibrotic disease in one aspect has or is suspected of having one or more risk factors for developing a fibrotic disease. Risk factors for fibrotic disease may include an individual's age (e.g., middle-age or older adults), the presence of inflammation, having one or more genetic component associated with development of a fibrotic disease, medical history such as treatment with a drug or procedure believed to be associated with an enhanced susceptibility to fibrosis (e.g., radiology) or a medical condition believed to be associated with fibrosis, a history of smoking, the presence of occupational and/or environmental factors such as exposure to pollutants associated with development of a fibrotic disease. In some embodiments, the individual at risk for developing a fibrotic disease is an individual who has or is suspected of having NAFLD, NASH, CKD, scleroderma, Crohn's Disease, NSIP, PSC, PBC, or is an individual who has had or is suspected of having had a myocardial infarction.

In some embodiments, the fibrotic disease is fibrosis of a tissue such as the lung (pulmonary fibrosis), the liver, the skin, the heart (cardiac fibrosis), the kidney (renal fibrosis), or the gastrointestinal tract (gastrointestinal fibrosis).

In some embodiments, the fibrotic disease is pulmonary fibrosis (such as IPF), liver fibrosis, skin fibrosis, scleroderma, cardiac fibrosis, renal fibrosis, gastrointestinal fibrosis, primary sclerosing cholangitis, or biliary fibrosis (such as PBC).

In some embodiments, the fibrotic disease is a pulmonary fibrosis, e.g., idiopathic pulmonary fibrosis (IPF). In some embodiments, the pulmonary fibrosis is, e.g., interstitial lung disease, radiation-induced pulmonary fibrosis, or systemic sclerosis associated interstitial lung disease.

In some embodiments, the fibrotic disease is a primary sclerosing cholangitis, or biliary fibrosis. In some embodiments, the fibrotic disease is primary biliary cholangitis (also known as primary biliary cirrhosis) or biliary atresia.

In some embodiments, the fibrotic disease is fibrotic nonspecific interstitial pneumonia (NSIP).

In some embodiments, the fibrotic disease is a liver fibrosis, e.g., infectious liver fibrosis (from pathogens such as HCV, HBV or parasites such as schistosomiasis), NASH, alcoholic steatosis induced liver fibrosis, and cirrhosis. In some embodiments, the liver fibrosis is nonalcoholic fatty liver disease (NAFLD). In some embodiments, the liver fibrosis is NASH.

In some embodiments, the fibrotic disease is biliary tract fibrosis.

In some embodiments, the fibrotic disease is renal fibrosis, e.g., diabetic nephrosclerosis, hypertensive nephrosclerosis, focal segmental glomerulosclerosis ("FSGS"), and acute kidney injury from contrast induced nephropathy. In several embodiments, the fibrotic disease is diabetic nephropathy, diabetic kidney disease, or chronic kidney disease.

In some embodiments, the fibrotic disease is characterized by one or more of glomerulonephritis, end-stage kidney disease, hearing loss, changes to the lens of the eye, hematuria, or proteinuria. In some embodiments, the fibrotic disease is Alport syndrome.

In some embodiments, the fibrotic disease is systemic and local sclerosis or scleroderma, keloids and hypertrophic scars, or post surgical adhesions. In some embodiments, the fibrotic disease is scleroderma or systemic sclerosis.

In some embodiments, the fibrotic disease is atherosclerosis or restenosis.

In some embodiments, the fibrotic disease is a gastrointestinal fibrosis, e.g., Crohn's disease.

In some embodiments, the fibrotic disease is cardiac fibrosis, e.g., post myocardial infarction induced fibrosis and inherited cardiomyopathy.

In some embodiments, methods may include modulating the activity of at least one integrin in an individual in need thereof. For example, the method may include modulating the activity of $\alpha_v\beta_6$. The method may include modulating the activity of $\alpha_v\beta_1$. The method may include modulating the activity of $\alpha_v\beta_1$ and $\alpha_v\beta_6$. Modulating the activity of the at least one integrin may include, e.g., inhibiting the at least one integrin. The method may include administering to the individual an amount of a crystalline form effective to modulate the activity of the at least one integrin in the individual, e.g., at least one of $\alpha_v\beta_1$ and $\alpha_v\beta_6$. The individual in need of modulating the activity of at least one integrin may have any of the fibrotic disease or conditions described herein. For example, the fibrotic disease or condition may include idiopathic pulmonary fibrosis, interstitial lung disease, radiation-induced pulmonary fibrosis, nonalcoholic fatty liver disease (NAFLD), nonalcoholic steatohepatitis (NASH), alcoholic liver disease induced fibrosis, Alport syndrome, primary sclerosing cholangitis, primary biliary cholangitis (also known as primary biliary cirrhosis), biliary atresia, systemic sclerosis associated interstitial lung disease, scleroderma (also known as systemic sclerosis), diabetic nephropathy, diabetic kidney disease, focal segmental glomerulosclerosis, chronic kidney disease, or Crohn's Disease. The method may include administering to the individual an amount of a crystalline form effective to modulate the activity of the at least one integrin in the individual, e.g., at least one of $\alpha_v\beta_1$ and $\alpha_v\beta_6$,the individual being in need of treatment for NASH. The method may include administering to the individual an amount of a crystalline form effective to modulate the activity of the at least one integrin in the individual, e.g., at least one of $\alpha_v\beta_1$ and $\alpha_v\beta_6$, the individual being in need of treatment for IPF.

The fibrotic disease may be mediated primarily by $\alpha_v\beta_6$, for example, the fibrotic disease may include idiopathic pulmonary fibrosis or renal fibrosis. Accordingly, the method may include modulating the activity of $\alpha_v\beta_6$ to treat conditions primarily mediated by $\alpha_v\beta_6$ such as IPF. The fibrotic disease may be mediated primarily by $\alpha_v\beta_1$, for example, the fibrotic disease may include NASH. Accordingly, the method may include modulating the activity of $\alpha_v\beta_1$ to treat conditions primarily mediated by $\alpha_v\beta_1$, e.g., NASH. The fibrotic disease may be mediated by $\alpha_v\beta_1$ and $\alpha_v\beta_6$,for example, the fibrotic disease may include PSC or biliary atresia. Accordingly, the method may include modulating the activity of $\alpha_v\beta_1$ and $\alpha_v\beta_6$ to treat conditions mediated by both $\alpha_v\beta_1$ and $\alpha_v\beta_6$.

The crystalline form may be a modulator, e.g., an inhibitor, of $\alpha_v\beta_1$. The crystalline form may be a modulator, e.g., an inhibitor, of $\alpha_v\beta_6$. The crystalline form may be a dual modulator, such as a dual inhibitor, e.g., dual selective inhibitor, of $\alpha_v\beta_1$ and $\alpha_v\beta_6$.

Modulating or inhibiting the activity of one or both of $\alpha_v\beta_1$ integrin and $\alpha_v\beta_6$ integrin, thereby treating an individual with a fibrotic disease, indicates that $\alpha_v\beta_1$ integrin, $\alpha_v\beta_6$ integrin, or $\alpha_v\beta_1$ integrin and $\alpha_v\beta_6$ integrin are modulated or inhibited to a degree sufficient to treat the fibrotic disease in the individual.

In some embodiments, provided is a crystalline form (e.g., Form I, Form II, Form III, or Form IV) for use in the treatment of a fibrotic disease. Also provided is use of a crystalline form (e.g., Form I, Form II, Form III, or Form IV) in the manufacture of a medicament for the treatment of a fibrotic disease.

In some embodiments, provided is a method of inhibiting $\alpha_v\beta_6$ integrin in an individual comprising administering a crystalline form disclosed herein (e.g., Form I, Form II, Form III, or Form IV).

Also provided is a method of inhibiting TGFβ activation in a cell comprising administering to the cell a crystalline form disclosed herein (e.g., Form I, Form II, Form III, or Form IV).

Also provided is a method of inhibiting $\alpha_v\beta_6$ integrin in an individual in need thereof, comprising administering to the individual a crystalline form disclosed herein (e.g., Form I, Form II, Form III, or Form IV). In one such method, the crystalline form is a selective $\alpha_v\beta_6$ integrin inhibitor. In another such method, the crystalline form does not inhibit substantially $\alpha_4\beta_1$, $\alpha_v\beta_8$ and/or $\alpha_2\beta_3$ integrin. In yet another such method, the crystalline form inhibits $\alpha_v\beta_6$ integrin but does not inhibit substantially $\alpha_4\beta_1$ integrin. In still another such method, the crystalline form inhibits $\alpha_v\beta_6$ integrin but does not inhibit substantially $\alpha_v\beta_8$ integrin. In a further such method, the crystalline form inhibits $\alpha_v\beta_6$ integrin but does not inhibit substantially $\alpha_2\beta_3$ integrin. In one embodiment is provided a method of inhibiting $\alpha_v\beta_6$ integrin and one or more of $\alpha_v\beta_1$, $\alpha_v\beta_3$, $\alpha_v\beta_5$, $\alpha_2\beta_1$, $\alpha_3\beta_1$, $\alpha_6\beta_1$, $\alpha_7\beta_1$ and $\alpha_{11}\beta_1$ integrin in an individual in need thereof. In another embodiment is provided a method of inhibiting $\alpha_v\beta_6$ integrin and $\alpha_v\beta_1$ integrin. In another embodiment is provided a method of inhibiting $\alpha_v\beta_6$ integrin, $\alpha_v\beta_3$ integrin and $\alpha_v\beta_5$ integrin. In another embodiment is provided a method of inhibiting $\alpha_v\beta_6$ integrin and $\alpha_2\beta_1$ integrin. In another embodiment is provided a method of inhibiting $\alpha_v\beta_6$ integrin, $\alpha_2\beta_1$ integrin and $\alpha_3\beta_1$ integrin. In another embodiment is provided a method of inhibiting $\alpha_v\beta_6$ integrin and $\alpha_6\beta_1$ integrin. In another embodiment is provided a method of inhibiting $\alpha_v\beta_6$ integrin and $\alpha_7\beta_1$ integrin. In another embodiment is provided a method of inhibiting $\alpha_v\beta_6$ integrin and $\alpha_{11}\beta_1$ integrin. In all such embodiments, in one aspect the method of inhibition is for an individual in need thereof, such as an individual who has or is suspected of having a fibrotic disease, and wherein the method comprises administering to the individual a crystalline form disclosed herein (e.g., Form I, Form II, Form III, or Form IV).

In any of the described methods, in one aspect the individual is a human, such as a human in need of the method. The individual may be a human who has been diagnosed with or is suspected of having a fibrotic disease. The individual may be a human who does not have detectable disease but who has one or more risk factors for developing a fibrotic disease.

Kits

In another aspect, provided is a kit comprising one or more crystalline forms disclosed herein (e.g., Form I, Form II, Form III, and/or Form IV) or a pharmaceutical composition comprising a crystalline forms as described herein. The kits may employ any of the crystalline forms disclosed herein. The kits may be used for any one or more of the uses described herein, and, accordingly, may contain instructions for use in the treatment of a fibrotic disease.

Kits generally comprise suitable packaging. The kits may comprise one or more containers comprising any compound described herein. Each component (if there is more than one component) can be packaged in separate containers or some components can be combined in one container where cross-reactivity and shelf life permit. One or more components of a kit may be sterile and/or may be contained within sterile packaging.

The kits may be in unit dosage forms, bulk packages (e.g., multi-dose packages) or sub-unit doses. For example, kits may be provided that contain sufficient dosages of a compound as disclosed herein (e.g., a therapeutically effective amount) and/or a second pharmaceutically active compound useful for a disease detailed herein (e.g., fibrosis) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the crystalline forms and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

EXAMPLES

The following examples are provided to further aid in understanding the embodiments disclosed in the application, and presuppose an understanding of conventional methods well known to those persons having ordinary skill in the art to which the examples pertain. The particular materials and conditions described hereunder are intended to exemplify particular aspects of embodiments disclosed herein and should not be construed to limit the reasonable scope thereof.

The following abbreviations may be used herein:

| XRPD | X-Ray Powder Diffraction |
|---|---|
| DSC | Differential Scanning Calorimetry |
| TGA | Thermogravimetric Analysis |
| DVS | Dynamic Vapor Sorption |
| equiv. or eq. | Equivalents |
| RH | Relative humidity |
| RT | Room temperature |
| MEK | Methyl ethyl ketone |
| IPAc | Isopropyl acetate |
| MIBK | 4-Methyl-2-pentanone |
| EtOH | Ethanol |
| DMSO | Dimethyl sulfoxide |
| TBME or MTBE | tert-Butyl methyl ether |
| THF | Tetrahydrofuran |
| 2-MeTHF | 2-Methyltetrahydrofuran |
| CPME | Cyclopentyl methyl ether |
| DCM | Dichloromethane |
| MeOH | Methanol |
| ACN | Acetonitrile |
| IPA | Isopropyl alcohol |
| TFA | Trifluoroacetic Acid |
| API | Active Pharmaceutical Ingredient |
| HPLC | High performance liquid chromatography |

The crystalline forms were characterized by various analytical techniques, including XRPD, DSC, TGA, DVS, $^{1}H$ NMR, and HPLC using the procedures described below.

XRPD

For XRPD analysis, unless otherwise stated, PANalytical Empyrean and X' Pert3 X-ray powder diffractometers were used. The XRPD parameters used are listed in the table below.

Parameters for XRPD Test

| Parameters | Empyrean | X' Pert3 |
|---|---|---|
| X-Ray wavelength | Cu, Kα; Kα1 (Å): 1.540598 Kα2 (Å): 1.544426 intensity ratio Kα2/Kα1: 0.50 | Cu, Kα; Kα1 (Å): 1.540598 Kα2 (Å): 1.544426 intensity ratio Kα2/Kα1: 0.50 |
| X-Ray tube setting | 45 kV, 40 mA | 45 kV, 40 mA |
| Divergence slit | Automatic | 1/8° |
| Scan mode | Continuous | Continuous |
| Scan range (2θ/°) | 3°~40° | 3°~40° |
| Step size (2θ/°) | 0.0167° | 0.0263° |
| Scan step time (s) | 17.780 | 46.665 |
| Test time (s) | About 5 min 30 s | About 5 min |

TGA and DSC

TGA data were collected using a TA Discovery5500/Q5000 TGA from TA Instruments. DSC was performed using a TA Discovery2500/Q2000 DSC from TA Instruments. Detailed parameters used are listed in the table below.

Parameters for TGA and DSC Test

| Parameters | TGA | DSC |
|---|---|---|
| Method | Ramp | Ramp |
| Sample pan | Aluminum, open | Aluminum, crimped/open |
| Temperature | RT- desired temperature | 25° C.-desired temperature |
| Heating rate | 10° C./min | 10° C./min |
| Purge gas | $N_2$ | $N_2$ |

DVS

DVS was measured via a SMS (Surface Measurement Systems) DVS Intrinsic. The relative humidity at 25° C. were calibrated against the deliquescence point of LiCl, $Mg(NO_3)_2$ and KCl. Parameters for DVS test are listed in the table below.

Parameters for DVS Test

| Parameters | DVS |
|---|---|
| Temperature | 25° C. |
| Sample size | 10~20 mg |
| Gas and flow rate | $N_2$, 200 mL/min |
| dm/dt | 0.002%/min |
| Min. dm/dtstabilityduration | 10 min |
| Max. equilibrium time | 180 min |
| RH range | 95% RH-0% RH-95% RH |
| RH step size | 10% (90% RH-0% RH-90% RH) |
| | 5% (95% RH-90% RH and 90% RH-95% RH) |

$^{1}H$ NMR $^{1}H$ NMR $^{1}H$ NMR was collected on a Bruker 400 MHz NMR spectrometer using D2O as solvent.

HPLC

Agilent HPLC was utilized and detailed chromatographic conditions for purity and stoichiometric ratio measurement are listed in the tables below.

Chromatographic Conditions and Parameters for Purity Test

| Parameters | Agilent 1260 DAD Detector | |
|---|---|---|
| Column | Waters XBridge column (4.6 × 150 mm, 3.5 μm) | |
| Mobile phase | A: $H_2O$ (0.1% TFA), B: ACN (0.1% TFA) | |
| Gradient table | Time (mm) | % B |
| | 0.0 | 5 |
| | 20.0 | 15 |
| | 30.0 | 30 |
| | 35.0 | 90 |
| | 38.0 | 90 |
| | 38.1 | 5 |
| | 45.0 | 5 |
| Run time | 45.0 min | |
| Post time | 0.0 min | |
| Flow rate | 1.0 mL/min | |
| Injection volume | 5 μL | |
| Detector wavelength | UV at 316 nm | |
| Column temperature | 40° C. | |
| Sampler temperature | 5° C. | |
| Diluent | $H_2O$:ACN = 9:1 | |

Chromatographic Conditions and Parameters for Stoichiometric Ratio Test

| Parameters | Agilent 1260 DAD Detector | |
|---|---|---|
| Column | Waters XBridge column (4.6 × 150 mm, 3.5 μm) | |
| Mobile phase | A: $H_2O$ (0.1% TFA), B: ACN (0.1% TFA) | |
| Gradient table | Time (min) | % B |
| | 0.0 | 10 |
| | 5.0 | 15 |
| | 7.0 | 30 |
| | 10.0 | 90 |
| | 11.0 | 90 |
| | 11.1 | 10 |
| | 15.0 | 10 |
| Run time | 15.0 min | |
| Post time | 0.0 min | |
| Flow rate | 1.0 mL/min | |
| Injection volume | 5 μL | |
| Detector wavelength | UV at 316 nm | |
| Column temperature | 40° C. | |
| Sampler temperature | 5° C. | |
| Diluent | $H_2O$:ACN = 9:1 | |

Example 1. Preparation of (S)-4-((2-methoxyethyl)(4-(5,6,7,8-tetrahydro-1,8-naphthyridin-2-yl)butyl)amino)-2-(quinazolin-4-ylamino)butanoic Acid (S)-4-((2-methoxyethyl)(4-(5,6,7,8-tetrahydro-1,8-naphthyridin-2-yl)butyl)amino)-2-(quinazolin-4-ylamino)butanoic acid may be prepared using the procedure disclosed in US 20190276449.

Example 2. Salt Studies

Salt screening experiments were performed under 150 conditions using 30 salt formers (including base and acid) in five distinct solvent systems (Table 5). Amorphous freeform and the corresponding salt formers were mixed in a molar ratio of 1:1 in five different solvent systems, and then stirred at RT for approximately 5 days. After centrifugation, the resulting solids were dried under vacuum at RT for 4 h, and then analyzed by XRPD.

A molar ratio of 1:2 (API/phosphoric acid) in five different solvent systems did not generate additional phosphate salt forms.

Example 3. Preparation of Form I from (S)-4-((2-methoxyethyl)(4-(5,6,7,8-tetrahydro-1,8-naphthyridin-2-yl)butyl)amino)-2-(quinazolin-4-ylamino)butanoic Acid Free Form Form I was prepared by mixing ~20 mg amorphous freeform of (S)-4-((2-methoxyethyl)(4-(5,6,7,8-tetrahydro-1,8-naphthyridin-2-yl)butyl)amino)-2-(quinazolin-4-ylamino)butanoic acid with 4.3 mg phosphoric acid (85%) and slurrying in EtOH at RT for 5 days. The product was analyzed by XRPD, DSC, TGA, $^1H$ NMR, and HPLC. The XRPD pattern is shown in FIG. 1A. The TGA and DSC graphs are shown in FIG. 1B. The TGA and DSC graphs showed a weight loss of 5.21% up to 150° C., and three endotherm peaks at 88.3, 136.3, and 197.6° C. $^1H$ NMR ($D_2O$) data showed 2.5% weight percentage of residual EtOH. Based on HPLC/IC analysis, the molar ratio of API:acid was 1:1.

Form I on 100 mg scale was obtained via slurrying of 99.5 mg amorphous freeform of (S)-4-((2-methoxyethyl)(4-(5,6,7,8-tetrahydro-1,8-naphthyridin-2-yl)butyl)amino)-2-(quinazolin-4-ylamino)butanoic acid and an equimolar amount of phosphoric acid (24.8 mg, 85%) in 2.5 mL EtOH at cycling temperature (50° C. to 5° C. at 0.05° C./min, then 5° C. to 50° C. at 0.375° C./min, three cycles). The product was analyzed by XRPD, DSC, TGA, $^1H$ NMR, and HPLC. The XRPD pattern is shown in FIG. 1A. The TGA and DSC graphs are shown in FIG. 1C. The TGA and DSC graphs showed a weight loss of 5.04% up to 110° C., and three endotherm peaks at 86.1, 140.8, and 197.0° C. $^1H$ NMR ($D_2O$) showed 0.4% weight percentage of residual EtOH. Based on HPLC/IC analysis, the molar ratio of API:phosphoric acid was 1:1.

Form I on 1 g scale was obtained via slurrying of 1.04 g amorphous freeform of (S)-4-((2-methoxyethyl)(4-(5,6,7,8-tetrahydro-1,8-naphthyridin-2-yl)butyl)amino)-2-(quinazolin-4-ylamino)butanoic acid and an equimolar amount of phosphoric acid (232.9 mg, 85%) in 25 mL anhydrous EtOH (≥99.7%) at RT with Form I seed. The product was analyzed by XRPD, DSC, TGA, $^1H$ NMR, and HPLC. The XRPD pattern is show in FIG. 1A. The TGA and DSC graphs are shown in FIG. 1D. The TGA and DSC graphs showed a weight loss of 10.23% up to 150° C., and three endotherm peaks at 77.3, 132.2, and 197.0° C. $^1H$ NMR ($D_2O$) showed 0.2% weight percentage of residual EtOH. Based on HPLC/IC analysis, the molar ratio of API:phosphoric acid was 1:0.9.

Form I on 4.5 g scale was obtained via slurrying 4.5 g amorphous freeform of (S)-4-((2-methoxyethyl)(4-(5,6,7,8-tetrahydro-1,8-naphthyridin-2-yl)butyl)amino)-2-(quinazolin-4-ylamino)butanoic acid and an equimolar amount of 85% phosphoric acid (1.05 g) in anhydrous EtOH (≥99.7%) (112 mL) at RT and seeded with around 1 wt % Form I seed. The product was analyzed by XRPD, DSC, TGA, DVS, $^1H$ NMR, and HPLC. The XRPD pattern is shown in FIG. 1A. The TGA and DSC graphs are shown in FIG. 1E. The TGA and DSC graphs showed a weight loss of 7.37% up to 150° C., and three endotherm peaks at 95.2, 134.1, and 200.9° C. $^1H$ NMR ($D_2O$) showed 2 wt % of residual EtOH. Based on HPLC/IC analysis, the molar ratio of API:phosphoric acid was 1:1. The DVS graph is shown in FIG. 1F. It showed 16.4% water absorption at 25° C./80% RH, and Form I was deliquescent after the DVS test.

Example 4. Preparation of Form I from (S)-4-((2-methoxyethyl)(4-(5,6,7,8-tetrahydro-1,8-naphthyridin-2-yl)butyl)amino)-2-(quinazolin-4-ylamino)butanoic Acid Zwitterion A process for preparing (S)-4-((2-methoxyethyl)(4-(5,6,7,8-tetrahydro-1,8-naphthyridin-2-yl)butyl)amino)-2-(quinazolin-4-ylamino)butanoic acid zwitterion (ZI) solution in ethanol and converting it to Form I is described below.

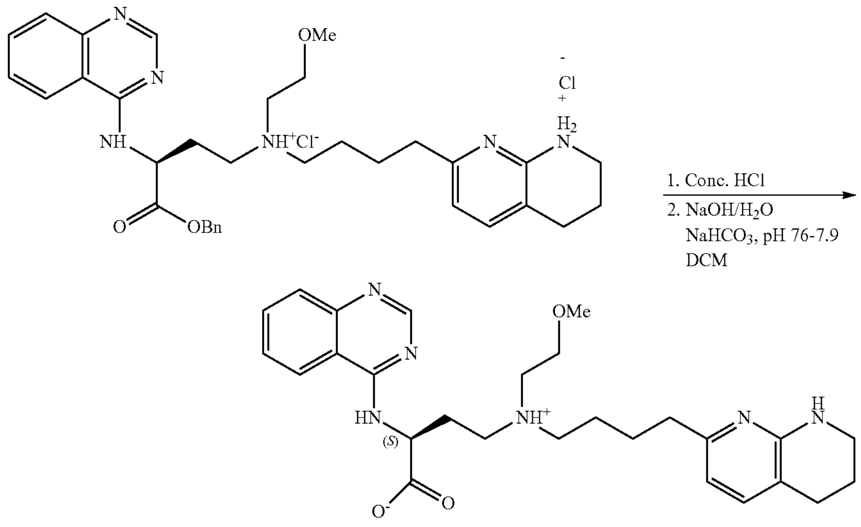

Benzyl (S)-4-((2-methoxyethyl)(4-(5,6,7,8-tetrahydro-1,8-naphthyridin-2-yl)butyl)amino)-2-(quinazolin-4-ylamino) butanoate·2HCl (1×, 1 equiv., bulk uncorrected for assay content) was dissolved in concentrated HCl (2.06×) and agitated at about 28° C. for about 18 h. The mixture was diluted with water and neutralized with NaOH (50%, equal equivalents to the HCl used) to give a mixture with pH ~7.2. The unreacted benzyl (S)-4-((2-methoxyethyl)(4-(5,6,7,8-tetrahydro-1,8-naphthyridin-2-yl)butyl)amino)-2-(quinazolin-4-ylamino)butanoate as well as impurities was removed by DCM extraction. Then $NaHCO_3$ (2 equiv.) was added as solid to give a mixture with pH 7.2-7.6 aqueous solution. TBME was used to further remove BnOH and trace impurities. ZI product is extracted out from the aqueous mixture using DCM. The wet product DCM solution was dried by azeotropic distillation of DCM followed by active carbon treatment and polish filtration. The product filtrate was concentrated under vacuum and chased with anhydrous ethanol to remove residual DCM. The final ZI was constituted with anhydrous ethanol to approximately 20 wt. % for subsequent crystallization. The overall yield was estimated in 84-89% (uncorrected from the starting material) with >98% AUC purity. The residual DCM was <0.4% and KF was <0.1% with residual sodium <250 ppm. This process was demonstrated on ~50 g scale.

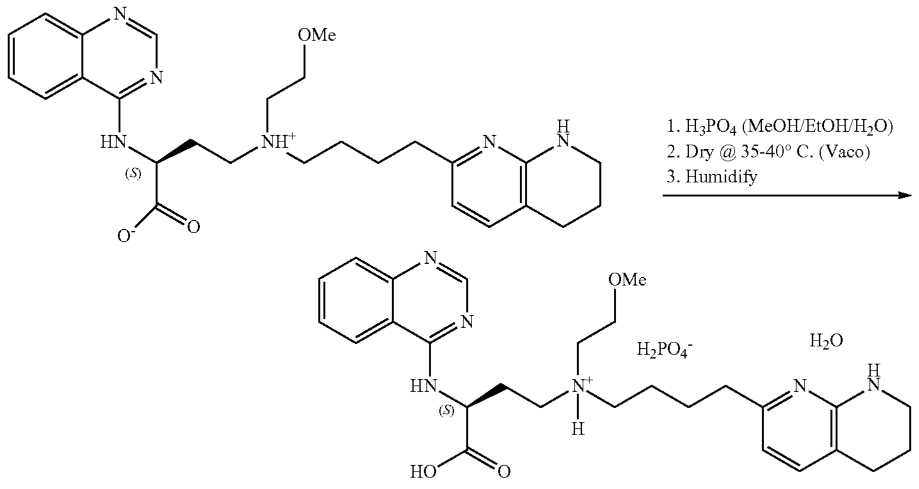

The (S)-4-((2-methoxyethyl)(4-(5,6,7,8-tetrahydro-1,8-naphthyridin-2-yl)butyl)amino)-2-(quinazolin-4-ylamino) butanoic acid ZI was dissolved in 1:4 MeOH/EtOH (v/v, 7.32× by weight). Phosphoric acid solution in 1:4 MeOH/EtOH (v/v, 0.25 eq to ZI) was added to the ZI solution at 30° C. slowly (with good mixing). Form I seed (2-3%) was added to give a suspension. Then, Form I was crystallized out gradually by dosing phosphoric acid solution in 1:4 MeOH/EtOH (0.8 equiv.) slowly (with good mixing). After complete addition of phosphoric acid, the batch was aged at 30° C. for a minimum 2 h and then at 20° C. for a minimum 2 h. The final product was filtered under vacuum with nitrogen protection followed by washing with pure EtOH. The wet product was dried under vacuum at 35-40° C., followed by conditioning the cake with humid $N_2$ (NMT 60% RH) at atmospheric pressure to give Form I crystals as off-white powder. The overall yield was in 85-90%, with >99% AUC product purity. Residual EtOH in product was <0.5 wt. % (spec: NMT 0.5 wt. %) and water content ~3%

(target 3±0.5 wt. % after humidification) as determined by Karl Fischer titration. This process was demonstrated at 40-50 g scale and applied to the 1.5 kg batch.

Example 5. Preparation of Form II from (S)-4-((2-methoxyethyl)(4-(5,6,7,8-tetrahydro-1,8-naphthyridin-2-yl)butyl)amino)-2-(quinazolin-4-ylamino)butanoic Acid Form II was prepared by mixing ~20 mg amorphous freeform of (S)-4-((2-methoxyethyl)(4-(5,6,7,8-tetrahydro-1,8-naphthyridin-2-yl)butyl)amino)-2-(quinazolin-4-ylamino)butanoic acid with 4.7 mg fumaric acid and slurrying in acetone/$H_2O$ (19:1, v:v) and temperature cycled (50° C. to 5° C. at 0.05° C./min, then 5° C. to 50° C. at 0.375° C./min, three cycles). The product was analyzed by XRPD. Form II was re-prepared on 100 mg scale via slurrying of 101.9 mg amorphous freeform of (S)-4-((2-methoxyethyl)(4-(5,6,7,8-tetrahydro-1,8-naphthyridin-2-yl)butyl)amino)-2-(quinazolin-4-ylamino)butanoic acid and 11.7 mg fumaric acid in 2.5 mL acetone/$H_2O$ (19:1, v:v) and temperature cycled (50° C. to 5° C. at 0.05° C./min, then 5° C. to 50° C. at 0.375° C./min, three cycles). The product was analyzed by XRPD, DSC, TGA, and $^1H$ NMR. XRPD patterns of Form II prepared on 20 mg scale and 100 mg scale are shown in FIG. 2A. The TGA and DSC graphs of Form II prepared on 100 mg scale are shown in FIG. 2B. The TGA and DSC graphs showed a weight loss of 13.02% up to 125° C., and one endotherm peak at 95.4° C. $^1H$ NMR ($D_2O$) data showed the molar ratio of API:fumaric acid was 1:0.6, and 1.9% weight percentage of residual acetone was observed.

Figure 2C:
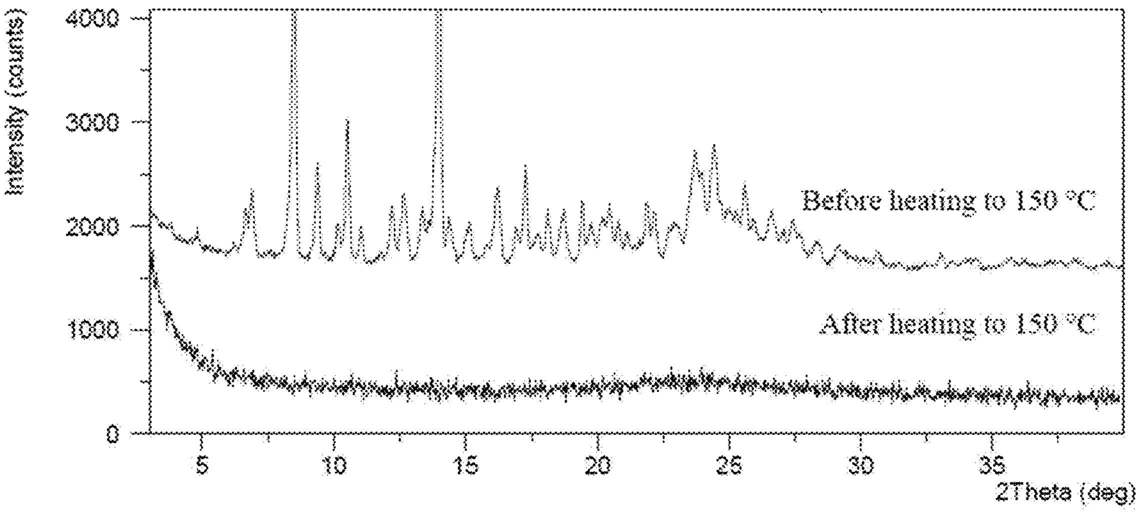
FIG. 2C shows a XRPD pattern of Form II before heating to 150° C. and a XRPD pattern of Form II after heating to 150° C. (top: before heating to 150° C.; bottom: after heating to 150° C.).

A heating experiment was performed on Form II and an amorphous sample was obtained after heating the sample to 150° C., as determined by XRPD. The XRPD results are shown in FIG. 2C.

Example 6. Preparation of Form III from (S)-4-((2-methoxyethyl)(4-(5,6,7,8-tetrahydro-1,8-naphthyridin-2-yl)butyl)amino)-2-(quinazolin-4-ylamino)butanoic Acid Form III was prepared by mixing ~20 mg amorphous freeform of (S)-4-((2-methoxyethyl)(4-(5,6,7,8-tetrahydro-1,8-naphthyridin-2-yl)butyl)amino)-2-(quinazolin-4-ylamino)butanoic acid with 16.9 mg 1,5-naphthalenedisulfonic acid and slurrying in EtOAc at RT for 5 days. The product was analyzed by XRPD, DSC, TGA, and $^1H$ NMR. The XRPD pattern of Form III is shown in FIG. 3A. The TGA and DSC graphs of Form III are shown in FIG. 3B. The TGA and DSC graphs showed a weight loss of 11.11% up to 150° C., and one endotherm peak at 103.4° C. $^1H$ NMR ($D_2O$) data showed that the molar ratio of API:acid was 1:1.1, and no signal of residual EtOAc was observed.

Example 7. Preparation of Form IV from (S)-4-((2-methoxyethyl)(4-(5,6,7,8-tetrahydro-1,8-naphthyridin-2-yl)butyl)amino)-2-(quinazolin-4-ylamino)butanoic Acid 100 mg of (S)-4-((2-methoxyethyl)(4-(5,6,7,8-tetrahydro-1,8-naphthyridin-2-yl)butyl)amino)-2-(quinazolin-4-ylamino)butanoic acid and 20 mg of phosphoric acid (1:1 mole ratio) were dissolved in a solution of 3.3 ml iPA and 4.0 ml MeOH. The clear solution was let evaporate at 50° C., and afforded crystalline solids. PXRD was collected on the bulk solids and some large plates were isolated to use for single-crystal X-ray Crystallographic studies.

Bruker D8 QUEST Single-crystal X-ray Diffractometer, equipped with high brightness IμS 3.0 microfocus (50 kV×1 mA) for Cu radiation (λ=1.54178 Å) and with PHOTON II Charge-Integrating Pixel Array Detector of superior speed, sensitivity, and accuracy, was used for screening/evaluation of crystals and for diffraction data collection. X-ray diffraction data were collected with a crystal cooled at 173 K. The crystal structure solved using this dataset was a monophosphate salt of (S)-4-((2-methoxyethyl)(4-(5,6,7,8-tetrahydro-1,8-naphthyridin-2-yl)butyl)amino)-2-(quinazolin-4-ylamino)butanoic acid and a mixed solvate of iPA and water, with salt:iPA:water=2:1:1 (mole ratio). A simulated XRPD pattern generated from the crystal structure matched the pattern of the bulk, indicating that the bulk solids and the single crystal had the same crystal structure. The experimental and simulated XRPD patterns are shown in FIG. 4.

The crystal data is provided in Table 6.

TABLE 6

| | | |
|---|---|---|
| Chemical formula | $C_{28.50}H_{44}N_6O_8P$ | |
| Formula weight | 629.66 g/mol | |
| Temperature | 173(2)K | |
| Wavelength | 1.54178 Å | |
| Crystal size | 0.020 × 0.080 × 0.100 mm | |
| Crystal habit | clear colourless small plate | |
| Crystal system | monoclinic | |
| Space group | P 1 211 | |
| Unit cell dimensions | a = 8.4932(3) Å | α = 90° |
| | b = 16.9945(7) $Å^3$ | β = 92.746(2)° |
| | c = 21.3671(7) $Å^3$ | γ = 90° |
| Volume | 3080.5(2) $Å^3$ | |
| Z | 4 | |
| Density (calculated) | 1.358 g/$cm^3$ | |
| Absorption coefficient | 1.291 $mm^{-1}$ | |
| F(000) | 1344 | |

Example 8. Solubility Study

The approximate solubility of (S)-4-((2-methoxyethyl)(4-(5,6,7,8-tetrahydro-1,8-naphthyridin-2-yl)butyl)amino)-2-(quinazolin-4-ylamino)butanoic acid was determined at RT. Approximately 2 mg of solids were added into a 3-mL glass vial. Different solvents were then added stepwise (50-50-200-700 μL for each step) into the vials and stirred until the solids were dissolved or a total volume of 1 mL was reached. The solubility results are provided in Table 7A.

TABLE 7A

| Solvent | Solubility (mg/mL) | Solvent | Solubility (mg/mL) |
|---|---|---|---|
| MeOH | S > 52.0 | MTBE | S < 2.0 |
| EtOH | S > 44.0 | THF | S > 32.0 |
| IPA | S > 48.0 | 2-MeTHF | 6.3 < S < 19.0 |
| Acetone | 6.3 < S < 19.0 | CPME | 2.6 < S < 8.7 |
| MEK | 22.0 < S < 44.0 | ACN | 1.9 < S < 6.3 |
| MIBK | 2.5 < S < 8.3 | n-Heptane | S < 2.2 |
| EtOAc | 2.1 < S < 7.0 | Toluene | 1.9 < S < 6.3 |
| IPAc | 2.3 < S < 7.7 | $H_2O$ | 6.0 < S < 18.0 |
| DMSO | S > 42.0 | DCM | S > 38.0 |
| Anisole | 16.0 < S < 32.0 | 1,4-Dioxane | S > 42.0 |

The approximate solubility of Form I was determined at RT. Approximately 2 mg of solids were added into 3-mL glass vials. Different solvents were then added stepwise (50-50-200-700 μL for each step) into the vials until the solids were dissolved or a total volume of 1 mL was reached. The solubility results are provided in Table 7B.

TABLE 7B

| Solvent | Solubility (mg/mL) | Solvent | Solubility (mg/mL) |
|---|---|---|---|
| MeOH | S > 52.0 | MTBE | S < 2.1 |
| EtOH | 2.3 < S < 7.7 | THF | S < 1.6 |
| IPA | S < 2.2 | 2-MeTHF | S < 2.1 |
| Acetone | S < 1.9 | CPME | S < 1.9 |
| MEK | S < 2.4 | ACN | S < 1.6 |
| MIBK | S < 2.8 | n-Heptane | S < 2.1 |
| EtOAc | S < 1.7 | Toluene | S < 2.2 |
| IPAc | S < 2.6 | $H_2O$ | S > 56.0 |
| DMSO | 6.0 < S < 18.0 | DCM | S < 2.8 |
| Anisole | 1.6 < S < 5.3 | 1,4-Dioxane | S < 1.7 |

Example 9. Polymorph Studies

One hundred polymorph screening experiments were performed on Form I via anti-solvent addition, slurrying at RT/50° C./temperature cycling, solid vapor diffusion, liquid vapor diffusion and slow evaporation.

Anti-solvent addition: About 20 mg of Form I were dissolved in 1 mL solvent. The solution was filtered using a PTFE membrane (pore size of 0.45 μM) to obtain a clear solution, then was magnetically stirred (~750 rpm), followed by slow addition of anti-solvent until either a precipitate appeared, or the total volume of anti-solvent reached 5 mL. The obtained precipitate was isolated for XRPD analysis.

Slurrying at RT: About 20 mg of Form I were suspended in 1 mL of the corresponding solvent in an HPLC vial. After the suspension was stirred magnetically (~750 rpm) for about 7 days at RT, the remaining solids were isolated for XRPD analysis.

Slurrying at 50° C.: About 20 mg of Form I were suspended in 1 mL of the corresponding solvent in an HPLC vial. After the suspension was stirred magnetically (~750 rpm) for about 7 days at 50° C., the obtained solid form was Form I.

Liquid vapor diffusion: About 15 mg of Form I were dissolved in 1 mL of an appropriate solvent in a 3 mL vial. The solution was filtered into another clean glass vial using a PTFE membrane (pore size of 0.45 μM) to obtain a clear solution. The glass vial containing the clear solution was then placed into a 20 mL vial with 4 mL of the corresponding volatile anti-solvent. The 20 mL vial was sealed with a cap and kept at RT allowing sufficient time for the organic vapor to interact with the solution. Clear solutions or gel samples were obtained.

Solid vapor diffusion: About 15 mg of Form I were weighed into a 3 mL glass vial. The 3 mL vial was then placed into a 20 mL vial with 4 mL of corresponding solvents. The 20 mL vial was sealed with a cap and kept at RT. The solids were isolated for XRPD analysis after 7 days.

Temperature cycling: About 20 mg of Form I were suspended in 1 mL of solvent in an HPLC vial. The suspension was stirred magnetically (~750 rpm) from 50° C. to 5° C. at 0.05° C./min, then from 5° C. to 50° C. at 0.375° C./min, which was repeated for three cycles. The solid forms obtained were amorphous and Form I.

Slow evaporation: About 15 mg of Form I were dissolved in 1 mL of solvent in a 3 mL glass vial. All samples were filtered using a PTFE membrane (pore size of 0.45 μM) and the filtrates were used for the follow up steps. The vials were sealed using Parafilm® (poked with several pin holes). Gel samples were obtained, and then the corresponding solvent was added and transferred to temperature cycling.

A heating experiment was performed on Form I. No form changes were observed for Form I after heating to 110° C., and an amorphous sample was obtained after heating to 150° C.

Example 9. Solid Phase Integrin $\alpha_v\beta_6$ Binding Assay

Microplates were coated with recombinant human integrin $\alpha_v\beta_6$ (2 μg/mL) in PBS (100 μL/well 25° C., overnight). The coating solution was removed, washed with wash buffer (0.05% Tween 20; 0.5 mM $MnCl_2$; in 1×TBS). The plate was blocked with 200 μL/well of Block Buffer (1% BSA; 5% sucrose; 0.5 mM $MnCl_2$; in 1×TBS) at 37° C. for 2 h. Dilutions of testing compounds and recombinant TGF$\beta_1$ LAP (0.67 μg/mL) in binding buffer (0.05% BSA; 2.5% sucrose; 0.5 mM $MnCl_2$; in 1×TBS) were added. The plate was incubated for 2 hours at 25° C., washed, and incubated for 1 hour with Biotin-Anti-hLAP. Bound antibody was detected by peroxidase-conjugated streptavidin. The $IC_{50}$ values for testing compounds were calculated by a four-parameter logistic regression. The $IC_{50}$ value obtained for $\alpha_v\beta_6$ integrin inhibition for (S)-4-((2-methoxyethyl)(4-(5,6,7,8-tetrahydro-1,8-naphthyridin-2-yl)butyl)amino)-2-(quinazolin-4-ylamino)butanoic acid was <50 nM.

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The invention claimed is:

1. A crystalline form of a phosphate salt of (S)-4-((2-methoxyethyl)(4-(5,6,7,8-tetrahydro-1,8-naphthyridin-2-yl)butyl)amino)-2-(quinazolin-4-ylamino)butanoic acid, wherein the crystalline form is characterized as having an XRPD pattern comprising a peak at an angle 2-theta of 4.31±0.2 degrees.

2. The crystalline form of claim 1, wherein the crystalline form is characterized as having an XRPD pattern comprising peaks at angles 2-theta of 4.31±0.2 and 6.76±0.2 degrees.

3. The crystalline form of claim 1, wherein the crystalline form is characterized as having:

a. endotherm peaks at about 88.3° C., about 136.3° C., and/or about 197.6° C., as determined by DSC;

b. endotherm peaks at about 86.1° C., about 140.8° C., and/or about 197.0° C., as determined by DSC;

c. endotherm peaks at about 77.3° C., 132.2° C., and/or about 197.0° C., as determined by DSC; or d. endotherm peaks at about 95.2° C., about 134.1° C., and/or about 200.9° C., as determined by DSC.

4. The crystalline form of claim 1, wherein the crystalline form is characterized as showing:

a. a weight loss of about 5.21% after heating from about 26.5° C. about 150.0° C., as determined by TGA, b. a weight loss of about 5.04% after heating from about 27.0° C. to about 110.0° C., as determined by TGA, c. a weight loss of about 10.32% after heating from about 30.0° C. to about 150.0° C., as determined by TGA, or d. a weight loss of about 7.37% after heating from about 27.0° C. to about 150.0° C., as determined by TGA.

5. The crystalline form of claim 1, wherein the crystalline form is a hydrate of the phosphate salt.

6. The crystalline form of claim 5, wherein the crystalline form is the phosphate salt and has a water content of about 3% by weight.

7. A crystalline form of a fumarate salt of (S)-4-((2-methoxyethyl)(4-(5,6,7,8-tetrahydro-1,8-naphthyridin-2-yl)butyl)amino)-2-(quinazolin-4-ylamino)butanoic acid, wherein the crystalline form is characterized as having an XRPD pattern comprising a peak at angle 2-theta of 8.47±0.2 degrees.

8. The crystalline form of claim 7, wherein the crystalline form is characterized as having an XRPD pattern comprising peaks at angles 2-theta of 8.47±0.2 and 10.52±0.2 degrees.

9. The crystalline form of claim 7, wherein the crystalline form is characterized as having an endotherm peak at about 95.4° C., as determined by DSC.

10. The crystalline form of claim 7, wherein the crystalline form is characterized as showing a weight loss of about 13.02% after heating from about 26.0° C. to about 125.0° C., as determined by TGA.

11. A crystalline form of a 1,5-naphthalenedisulfonate salt of (S)-4-((2-methoxyethyl)(4-(5,6,7,8-tetrahydro-1,8-naphthyridin-2-yl)butyl)amino)-2-(quinazolin-4-ylamino)butanoic acid, wherein the crystalline form is characterized as having an XRPD pattern comprising a peak at an angle 2-theta of 12.58±0.2 degrees.

12. The crystalline form of claim 11, wherein the crystalline form is characterized as having an endotherm peak at about 103.4° C., as determined by DSC.

13. The crystalline form of claim 11, wherein the crystalline form is characterized as showing a weight loss of about 11.11% after heating from about 23.0° C. to about 150.0° C., as determined by TGA.

14. The crystalline form of claim 7, wherein the crystalline form has a water content of less than about 0.5% by weight.

15. The crystalline form of claim 14, wherein the crystalline form is anhydrous.

16. A pharmaceutical composition comprising the crystalline form of claim 1, and a pharmaceutically acceptable carrier or excipient.

17. A kit comprising the crystalline form of claim 1.

18. The kit of claim 17, further comprising instructions for the treatment of a fibrotic disease, wherein the fibrotic disease is selected from the group consisting of: idiopathic pulmonary fibrosis, liver fibrosis, skin fibrosis, cardiac fibrosis, kidney fibrosis, gastrointestinal fibrosis, primary sclerosing cholangitis, and biliary fibrosis.

19. A method of inhibiting $\alpha_v\beta_6$ integrin in an individual comprising administering to the individual the crystalline form of claim 1.

20. A method of inhibiting TGFB activation in a cell comprising administering to the cell the crystalline form of claim 1.

21. The crystalline form of claim 11, wherein the crystalline form has a water content of less than about 0.5% by weight.

22. The crystalline form of claim 21, wherein the crystalline form is anhydrous.

23. A pharmaceutical composition comprising the crystalline form of claim 7, and a pharmaceutically acceptable carrier or excipient.

24. A pharmaceutical composition comprising the crystalline form of claim 11, and a pharmaceutically acceptable carrier or excipient.

25. A method of treating a fibrotic disease in an individual in need thereof comprising administering to the individual the crystalline form of claim 1, wherein the fibrotic disease is selected from the group consisting of: idiopathic pulmonary fibrosis (IPF), interstitial lung disease, radiation-induced pulmonary fibrosis, nonalcoholic fatty liver disease (NAFLD), nonalcoholic steatohepatitis (NASH), alcoholic liver disease induced by fibrosis, Alport syndrome, primary sclerosing cholangitis (PSC), primary biliary cholangitis, biliary atresia, systemic sclerosis associated interstitial lung disease, scleroderma, diabetic nephropathy, diabetic kidney disease, focal segmental glomerulosclerosis, chronic kidney disease, and Crohn's Disease.

26. A method of treating a fibrotic disease in an individual in need thereof comprising administering to the individual the crystalline form of claim 1, wherein the fibrotic disease is idiopathic pulmonary fibrosis, liver fibrosis, cardiac fibrosis, primary sclerosing cholangitis, or biliary fibrosis.

* * * * *